US012773389B2

(12) United States Patent
Hansen et al.

(10) Patent No.: US 12,773,389 B2
(45) Date of Patent: Oct. 27, 2026

(54) PULSATILE DRUG DELIVERY SYSTEM FOR TREATING MORNING AKINESIA

(71) Applicant: CONTERA PHARMA A/S, Hørsholm (DK)

(72) Inventors: John Bondo Hansen, Copenhagen Ø (DK); Mikael Søndergård Thomsen, Hvidovre (DK); Ann Vivian Fullerton, Copenhagen K (DK); Bent Højgaard, Allerød (DK); Peter Gudmund Nielsen, Vaerløse (DK)

(73) Assignee: CONTERA PHARMA A/S, Horsholm (DK)

( * ) Notice: Subject to any disclaimer, the term of this patent is extended or adjusted under 35 U.S.C. 154(b) by 0 days.

(21) Appl. No.: 19/299,911

(22) Filed: Aug. 14, 2025

(65) Prior Publication Data

US 2025/0367123 A1 Dec. 4, 2025

Related U.S. Application Data

(60) Continuation of application No. 17/930,169, filed on Sep. 7, 2022, now abandoned, which is a division of application No. 16/316,698, filed as application No. PCT/EP2017/067348 on Jul. 11, 2017, now Pat. No. 11,975,104.

(30) Foreign Application Priority Data

Jul. 11, 2016 (DK) ........................... PA 2016 70516

(51) Int. Cl.

| | |
|---|---|
| ***A61K 31/165*** | (2006.01) |
| ***A61K 9/16*** | (2006.01) |
| ***A61K 9/20*** | (2006.01) |
| ***A61K 9/28*** | (2006.01) |
| ***A61K 9/48*** | (2006.01) |
| ***A61K 31/194*** | (2006.01) |
| ***A61K 31/195*** | (2006.01) |
| ***A61K 31/198*** | (2006.01) |
| ***A61K 45/06*** | (2006.01) |
| ***A61P 25/16*** | (2006.01) |

(52) U.S. Cl.

CPC .......... *A61K 9/2081* (2013.01); *A61K 9/1652* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2077* (2013.01); *A61K 9/2086* (2013.01); *A61K 9/2866* (2013.01); *A61K 9/4808* (2013.01); *A61K 31/165* (2013.01); *A61K 31/194* (2013.01); *A61K 31/195* (2013.01); *A61K 31/198* (2013.01); *A61K 45/06* (2013.01); *A61P 25/16* (2018.01)

(58) Field of Classification Search

None

See application file for complete search history.

(56) References Cited

U.S. PATENT DOCUMENTS

| | | | |
|---|---|---|---|
| 3,253,023 | A | 5/1966 | Wysong |
| 3,717,634 | A | 2/1973 | Wu et al. |
| 3,976,776 | A | 8/1976 | Wu et al. |
| 4,166,452 | A | 9/1979 | Generales, Jr. |
| 4,182,763 | A | 1/1980 | Casten et al. |
| 4,265,874 | A | 5/1981 | Bonsen et al. |
| 4,356,108 | A | 10/1982 | Schwab et al. |
| 4,438,119 | A | 3/1984 | Allen et al. |
| 4,640,921 | A | 2/1987 | Othmer et al. |
| 4,687,772 | A | 8/1987 | Alderdice |
| 4,777,173 | A | 10/1988 | Shrotryia et al. |
| 4,832,957 | A | 5/1989 | Dempski et al. |
| 5,185,329 | A | 2/1993 | Gawin et al. |
| 5,288,501 | A | 2/1994 | Nuernberg et al. |
| 5,431,922 | A | 7/1995 | Nicklasson |
| 5,466,699 | A | 11/1995 | Robertson et al. |
| 5,484,788 | A | 1/1996 | Sharpe et al. |
| 5,633,009 | A | 5/1997 | Kenealy et al. |
| 5,637,314 | A | 6/1997 | Sharpe et al. |
| 5,705,506 | A | 1/1998 | Merlet et al. |
| 6,150,365 | A | 11/2000 | Mayol |
| 6,432,956 | B1 | 8/2002 | Dement et al. |
| 6,500,867 | B1 | 12/2002 | Virkki et al. |
| 6,627,223 | B2 | 9/2003 | Percel et al. |
| 6,750,237 | B1 | 6/2004 | Dearn et al. |
| 7,048,945 | B2 | 5/2006 | Percel et al. |
| 7,094,427 | B2 | 8/2006 | Han et al. |

(Continued)

FOREIGN PATENT DOCUMENTS

| | | | |
|---|---|---|---|
| DE | 10353657 | A1 | 6/2005 |
| WO | 00/06161 | A1 | 2/2000 |

(Continued)

OTHER PUBLICATIONS

Andrade et al., “Biologic data of macaca mulatta, macaca fascicularis, and saimiri sciureus used for research at the Fiocruz primate center”, Memórias do Instituto Oswaldo Cruz, 2004, vol. 99, No. 6, pp. 581-589.
Author Unknown, “Use of lactose in hard gelatin capsules”, DFE Pharma Brochure, 2011, pp. 1-8.
Bonifati et al., “Buspirone in levodopa-induced dyskinesias”, Clinical Neuropharmacology, 1994, vol. 17, No. 1, pp. 73-82.
Bristol-Myers Squibb Company, BuSpar® Patient Instruction Sheet, Nov. 2010, pp. 1-21.
Camargo et al., “The molecular mechanism of intestinal levodopa absorption and its possible implications for the treatment of Parkinson’s disease”, Journal of Pharmacology and Experimental Therapeutics, 2014, vol. 351, pp. 114-123.

(Continued)

*Primary Examiner* — Jake M Vu
(74) *Attorney, Agent, or Firm* — BakerHostetler

(57) ABSTRACT

Provided herewith is a pharmaceutical composition comprising, separately or together, a pulsatile release component comprising levodopa and a DOPA decarboxylase inhibitor for the management of OFF-time episodes in patients with Parkinson’s disease.

10 Claims, 10 Drawing Sheets

(56) References Cited

U.S. PATENT DOCUMENTS

| | | | |
|---|---|---|---|
| 7,220,767 B2 | 5/2007 | Dearn et al. | |
| 7,470,435 B2 | 12/2008 | Dixit et al. | |
| 8,329,734 B2 | 12/2012 | Aung-Din | |
| 8,377,474 B2 | 2/2013 | Hsu et al. | |
| 8,454,998 B2 | 6/2013 | Hsu et al. | |
| 8,557,283 B2 | 10/2013 | Hsu et al. | |
| 8,771,730 B2 | 7/2014 | Navon et al. | |
| 9,072,663 B2 | 7/2015 | Navon et al. | |
| 9,089,607 B2 | 7/2015 | Hsu et al. | |
| 9,089,608 B2 | 7/2015 | Hsu et al. | |
| 2001/0046964 A1 | 11/2001 | Percel et al. | |
| 2003/0035839 A1 | 2/2003 | Hirsh et al. | |
| 2003/0224045 A1 | 12/2003 | Han et al. | |
| 2004/0166159 A1 | 8/2004 | Han et al. | |
| 2006/0003005 A1 | 1/2006 | Cao et al. | |
| 2007/0173536 A1 | 7/2007 | Van et al. | |
| 2007/0249621 A1 | 10/2007 | Wolf et al. | |
| 2007/0270449 A1 | 11/2007 | Barlow et al. | |
| 2007/0275060 A1 | 11/2007 | Befumo et al. | |
| 2008/0069874 A1 | 3/2008 | Hall et al. | |
| 2008/0118556 A1 | 5/2008 | Devane et al. | |
| 2008/0125413 A1 | 5/2008 | Burgey et al. | |
| 2008/0166407 A1 | 7/2008 | Shalaby et al. | |
| 2008/0226715 A1 | 9/2008 | Cha et al. | |
| 2010/0105783 A1 | 4/2010 | Lee et al. | |
| 2010/0316712 A1* | 12/2010 | Nangia | A61K 9/5031 514/567 |
| 2011/0318321 A1 | 12/2011 | Selva et al. | |
| 2013/0195973 A1 | 8/2013 | Gupta et al. | |
| 2014/0221385 A1 | 8/2014 | Hansen et al. | |
| 2015/0157579 A1 | 6/2015 | Went et al. | |

FOREIGN PATENT DOCUMENTS

| | | | |
|---|---|---|---|
| WO | 02/44159 A2 | 6/2002 | |
| WO | 02/53139 A2 | 7/2002 | |
| WO | 03/11255 A1 | 2/2003 | |
| WO | 03/24960 A1 | 3/2003 | |
| WO | 2005/034908 A2 | 4/2005 | |
| WO | 2006/027681 A1 | 3/2006 | |
| WO | 2007/129329 A2 | 11/2007 | |
| WO | 2007/144422 A2 | 12/2007 | |
| WO | 2008/047839 A1 | 4/2008 | |
| WO | 2008/110577 A1 | 9/2008 | |
| WO | 2009/098661 A1 | 8/2009 | |
| WO | 2009/118167 A1 | 10/2009 | |
| WO | 2009/156380 A1 | 12/2009 | |
| WO | 2010/044736 A1 | 4/2010 | |
| WO | 2011/079313 A1 | 6/2011 | |
| WO | 2012/048710 A1 | 4/2012 | |
| WO | WO-2012059815 A1 * | 5/2012 | A61K 9/7007 |
| WO | 2012/163365 A1 | 12/2012 | |
| WO | 2016/115223 A1 | 7/2016 | |

OTHER PUBLICATIONS

Creed et al., "Contribution of decreased serotonin release to the antidyskinetic effects of deep brain stimulation in a rodent model of tardive dyskinesia: comparison of the subthalamic and entopeduncular nuclei", Journal of Neuroscience, 2012, vol. 32, No. 28, pp. 9574-9581.

Dekundy et al., "Modulation of L-DOPA-induced abnormal involuntary movements by clinically tested compounds: further validation of the rat dyskinesia model", Behavioural Brain Research, 2007, vol. 179, pp. 76-89.

Deleu, "The effect of carbidopa and entacapone pretreatment on the L-Dopa pharmacokinetics and metabolism in blood plasma and skeletal muscle in beagle dog: an in vivo microdialysis study", Journal of Pharmacology and Experimental Therapeutics, 1995, vol. 273, No. 3, pp. 1323-1331.

Emre, "Practical guidance for the management of Parkinson's disease with levodopa", ACNR, 2009, vol. 9, No. 2, pp. 26-29.

Eskow et al., "The partial 5-HT1A agonist buspirone reduces the expression and development of L-DOPA-induced dyskinesia in rats and improves L-DOPA efficacy", Pharmacology Biochemistry and Behavior, 2007, vol. 87, pp. 306-314.

Garg et al., "Progress in controlled gastroretentive delivery systems", Tropical Journal of Pharmaceutical Research, 2008, vol. 7, No. 3, pp. 1055-1066.

Gregoire et al., "Low doses of sarizotan reduce dyskinesias and maintain antiparkinsonian efficacy of L-Dopa in parkinsonian monkeys", Parkinsonism & Related Disorders, 2009, vol. 15, No. 6, pp. 445-452.

Guidance for Industry—Dissolution Testing of Immediate Release Solid Ora! Dosage Forms, U.S. Department of Health and Human Services, Food and Evaluation and Research (CDER), Aug. 1997, 17 pages.

Guidance for Industry-Extended Release Oral Dosage Forms: Development, Evaluation, and Application of In Vitro/In Vivo Correlations, U.S. Department of Health and Human Services, Food and Drug Administration, Center for Drug Evaluation and Research (CDER), Sep. 1997, 27 pages.

Haddad et al., "Dopamine and levodopa prodrugs for the treatment of Parkinson's disease", Molecules, 2017, pp. 1-17.

Hasegawa et al., Japanese Journal of Medicine and Pharmaceutical Science, 2007, 57(3), 313-317.

Hauser, "Future treatments for Parkinson's disease: surfing the PD pipeline", International Journal of Neuroscience, 2011, vol. 121, pp. 53-62.

Huot et al., "Anatomically selective serotonergic type 1A and serotonergic type 2A therapies for Parkinson's disease: an approach to reducing dyskinesia without exacerbating parkinsonism?", Journal of Pharmacology and Experimental Therapeutics, 2011, vol. 339, No. 1, pp. 2-8.

Huot et al., "L-745,870 reduces L-DOPA-induced dyskinesia in the 1-methyl-4-phenyl-1,2,3,6-tetrahydropyridine-lesioned macaque model of Parkinson's disease", Journal of Pharmacology and Experimental Therapeutics, 2012, vol. 342, No. 2, pp. 576-585.

Huot et al., "The pharmacology of L-DOPA-induced dyskinesia in Parkinson's disease", Pharmacological Reviews, 2013, vol. 65, pp. 171-222.

Ilhan et al., "Mini tablets: a short review-revision", Journal of Medical Chemical Research, 2017, vol. 3, No. 1, pp. 12-22.

Isaacson et al., "Morning akinesia and the potential role of gastroparesis—managing delayed onset of first daily dose of oral levodopa in patients with Parkinson's disease", European Neurological Review, 2013, pp. 82-84.

Jain et al., "Recent technologies in pulsatile drug delivery systems", Biomatter, 2011, vol. 1, No. 1, pp. 57-65.

Kannari et al., "Tandospirone citrate, a selective 5-HT1A agonist, alleviates L-DOPA-induced dyskinesia in patients with Parkinson's disease", Brain and Nerve, 2002, vol. 54, No. 2, pp. 133-137.

Khor et al., "The pharmacokinetics and pharmacodynamics of levodopa in the treatment of Parkinson's disease", Current Clinical Pharmacology, 2007, vol. 2, pp. 234-243.

Kleedorfer et al., "Buspirone in the treatment of levodopa induced dyskinesias", Journal of Neurology, Neurosurgery, and Psychiatry, 1991, vol. 54, pp. 376-377.

Leppert et al., "The effects of carbidopa dose and time and route of administration on systemic L-dopa levels in rats", Pharmaceutical Research, 1998, vol. 5, No. 9, pp. 587-591.

Ludwig et al., "Buspirone, Parkinson's disease, and the locus ceruleus", Clinical Neuropharmacology, 1986, vol. 9, No. 4, pp. 373-378.

Martin et al., "Receptor specificity and trigemino-vascular inhibitory actions of a novel 5-HT 1B/1D receptor partial agonist, 311 C90 (zolmitriptan)", British Journal of Pharmacology, 1997, vol. 121, pp. 157-164.

Metman et al., "Gastroretentive carbidopa/levodopa, DM-1992, for the treatment of advanced Parkinson's disease", Movement Disorders, 2015, vol. 30, No. 9, pp. 1222-1228.

Mohanachandran et al., "Superdisintegrants—an overview", International Journal of Pharmaceutical Sciences Review and Research, 2011, vol. 6, No. 1, pp. 105-109.

(56) References Cited

OTHER PUBLICATIONS

Naidu et al., "Effect of 5-HT1A and 5-HT2A-2C receptor modulation on neuroleptic-induced vacuous chewing movements", European Journal of Pharmacology, 2001, vol. 428, No. 1, pp. 81-86.
Patil et al., "Patented pulsatile drug delivery technologies for chronotherapy", Expert Opinion on Therapeutic Patents, 2014, vol. 24, No. 8, pp. 845-856.
Patwekar et al., "Controlled release approach to novel multiparticulate drug delivery system", International Journal of Pharma and Pharmaceutical Sciences, 2012, vol. 4, No. 3, pp. 757-763.
Priyanka, "A comprehensive review on pharmaceutical mini tablets", Journal of Drug Delivery and Therapeutics, 2018, vol. 8, No. 6, pp. 382-390.
Rajput et al., "Pulsatile drug delivery system: a review", International Research Journal of Pharmaceutical and Biomedical Sciences, 2012, vol. 3, No. 1, pp. 118-124.
Rikita et al., "Pulsatile drug delivery system: a review", International Research Journal of Pharmacy, 2012, vol. 3, No. 7, pp. 103-107.
Rose et al., "Peripheral pharmacokinetic handling and metabolism of L-dopa in the rat: the effect of route of administration and carbidopa pretreatment", Journal of Pharmacy and Pharmacology, 1991, vol. 43, pp. 325-330.
Rosengarten et al., "The effect of chronic administration of sarizotan, 5-HT1A agonist/D3/D4 ligand, on haloperidol-induced repetitive jaw movements in rat model of tardive dyskinesia", Progress in Neuro-Psychopharmacology and Biological Psychiatry, 2006, vol. 30, pp. 273-279.
Tambasco et al., "Morning akinesia in Parkinson's disease: challenges and solutions", Journal of Parkinsonism and Restless Legs Syndrome, 2016, vol. 6, pp. 57-63.
Westberg, https://www.pharmaexcipients.com/wp-content/uploads/2019/04/characterization-of-minitablets-1.pdf, Year 2019.
Yin, "A new formula for analyzing formulation patent obviousness", Temple Law Review, 2011, vol. 83, No. 3, pp. 829-856.
Dolhun, "Levodopa 2.0: New Strategies to Even Out the Peaks and Valleys", The Michael J. Fox Foundation for Parkinson's Research | Levodopa 2.0: New Strategies to Even Out the Peaks and Valleys, May 18, 2015, pp. 1-5.
Nutt, "Pharmacokinetics and Pharmacodynamics of Levodopa", Movement Disorders, vol. 23, Suppl. 3, 2008, pp. S580-S584.

* cited by examiner

PULSATILE DRUG DELIVERY SYSTEM FOR TREATING MORNING AKINESIA

CROSS REFERENCE TO RELATED APPLICATIONS

This application is a continuation of U.S. application Ser. No. 17/930,169, filed Sep. 7, 2022, which is a divisional of U.S. application Ser. No. 16/316,698, filed Jan. 10, 2019, now U.S. Pat. No. 11,975,104, which is the National Stage Entry of International Application No. PCT/EP2017/067348, filed Jul. 11, 2017, which claims the benefit of Danish Application PA 2016 70516, filed Jul. 11, 2016, the entireties of which are incorporated by reference herein.

TECHNICAL FIELD

The present invention relates to a pulsatile drug delivery system that enables a delayed burst release of levodopa and DOPA decarboxylase inhibitors including carbidopa in the small intestine, thereby providing for improved management of morning akinesia in Parkinson's disease patients.

BACKGROUND

Movement disorders are frequently caused by impaired regulation of dopamine neurotransmission. Parkinson's disease (PD) is an example of a movement disorder associated with dysfunctional regulation of dopamine neurotransmission, which is caused by progressive degeneration of dopamine neurons. In order to replace the lost dopamine PD motor symptoms is currently treated with oral levodopa (L-DOPA, a precursor of dopamine), which must be emptied from the stomach and absorbed in the proximal small intestine. Levodopa is converted into dopamine in the brain, and stored in the neurons until needed by the body for movement. It remains the single most effective agent in the management of Parkinson's symptoms.

Most PD patients treated with levodopa have motor fluctuations. An improvement in symptoms after L-DOPA administration is defined as "ON", whereas a return to symptoms is termed "OFF", i.e. when levodopa plasma concentration decreases. OFF periods generally appear when the benefit from a given levodopa dose disappears prematurely (wearing OFF) or when the next L-DOPA dose produces a delayed onset of action (delayed ON).

Motor complications of PD have been reported to occur after a few years of treatment with levodopa, whereby the long duration response becomes replaced by a short duration response, and OFF periods emerge. While OFF periods can be treated with several adjunctive medications, delayed onset of the next levodopa dose can significantly increase OFF period duration.

Morning akinesia is a delayed ON of the first L-DOPA daily dose, occurring in almost 60% of patients on dopaminergic treatment. This is primarily a motor symptom, but has been recently recognized as being correlated with nonmotor fluctuations.

Morning akinesia can significantly affect quality-of-life in PD patients, impairing the ability to perform basic daily activities.

Standard oral levodopa treatment is inadequate for the treatment of morning akinesia for reasons related to its pharmacodynamics and pharmacokinetics and because of its short half-life, erratic gastrointestinal absorption, and competitive transport across the blood-brain barrier. One of the first strategies attempted to focus on prolonging levodopa plasma levels, using long-acting, controlled-release levodopa preparations. Nevertheless, due to delayed gastric emptying, an oral dose of L-DOPA may remain in the stomach for a long time before being absorbed in the small intestine. Another approach is administering levodopa as a liquid solution to reduce gastric transit time and improve the onset of effect. This approach may be beneficial for some patients with severe fluctuations; however, the clinical benefits of liquid levodopa compared with tablets have not been confirmed in controlled clinical studies. To manage early morning akinesia and episodes of nocturnal hypomobility, many patients use L-DOPA on an intermittent or as-needed basis. However, the slow or unpredictable onset of effect limits the clinical benefit.

Alternative delivery of dopaminergic therapy by a non-oral route, such as subcutaneous apomorphine injection is used by patients with PD in the OFF state to decrease time-to-ON. However, an early morning subcutaneous self-pen injection in disabled advanced PD patients could be troublesome. Nasal, pulmonal and sublingual formulations of levodopa are also available.

Levodopa is almost always given in combination with DOPA decarboxylase inhibitors such as carbidopa that prevents the breakdown of levodopa before it can reach the brain and take effect; carbidopa enables a much lower dose of levodopa (80% less) and helps reduce the side effects of nausea and vomiting. Carbidopa/levodopa tablets are available in immediate-release (IR) and extended-release (ER) forms as well as dissolvable tablets that are placed under the tongue. A small, portable infusion pump delivers carbidopa and levodopa directly into the small intestine.

ER combination formulations maintain plasma levodopa concentrations in the therapeutic window for a prolonged time, providing greater ON time for patients and better home management and mobility; but it has not been established that the ER formulation improves dyskinesias or total sickness impact profile (SIP) scores.

It has been suggested that pretreatment with carbidopa prior to levodopa in some instances increases levodopa plasma AUC compared to simultaneous administration (see e g. Leppert et al. 1988).

Morning akinesia is one of the most common and earliest motor complications in PD patients, affecting almost all stages of the disease. There remains an unmet medical need to improve the night time sleeping pattern and morning akinesia in patients with Parkinson's disease in a safe, non-invasive and compliant manner.

SUMMARY

The present inventors have developed a pharmaceutical composition that addresses short-comings of current formulations comprising levodopa and DOPA decarboxylase inhibitors; by providing a composition that enables timed pulsatile release of these compounds. Providing a delayed burst release of a DOPA decarboxylase inhibitor such as carbidopa and a delayed burst release of levodopa after a predetermined lag time, preferably separated in time whereby the DOPA decarboxylase inhibitor is released before levodopa, provides a means for the management of morning akinesia in patients with Parkinson's disease.

With the disclosed pulsatile drug delivery, the patient may improve the night time sleeping pattern and be efficiently relieved from a complete disabling state in the morning. Furthermore, such a composition can be taken together with existing marketed immediate and controlled release levodopa products, to provide a full day dose coverage for most patients with Parkinson's disease.

It is an aspect to provide a pulsatile release pharmaceutical composition comprising levodopa and a DOPA decarboxylase inhibitor, and a pulsatile release component providing for a predetermined lag time followed by a pulse release of said levodopa and said DOPA decarboxylase inhibitor.

It is also an aspect to provide a pulsatile release pharmaceutical composition comprising, separately or together, a. a first pulsatile release component comprising levodopa, said first pulsatile release component providing for a predetermined lag time followed by a pulse release of levodopa, and b. a second pulsatile release component comprising a DOPA decarboxylase inhibitor, said second pulsatile release component providing for a predetermined lag time followed by a pulse release of said DOPA decarboxylase inhibitor, wherein in one embodiment the lag time of said first pulsatile release component comprising levodopa is longer than the lag time of said second pulsatile release component comprising a DOPA decarboxylase inhibitor.

In one embodiment said DOPA decarboxylase inhibitor is selected from the group consisting of carbidopa, benserazide, methyldopa and DFMD (α-Difluoromethyl-DOPA), or a pharmaceutically acceptable derivative thereof.

In one embodiment said pharmaceutical composition is a multiparticulate dosage form.

In one embodiment said pharmaceutical composition comprises, separately or together, one or more further active pharmaceutical ingredients.

In one embodiment said pharmaceutical composition is for use in the treatment of morning akinesia in a patient with Parkinson's disease.

DETAILED DESCRIPTION

Figure 1:
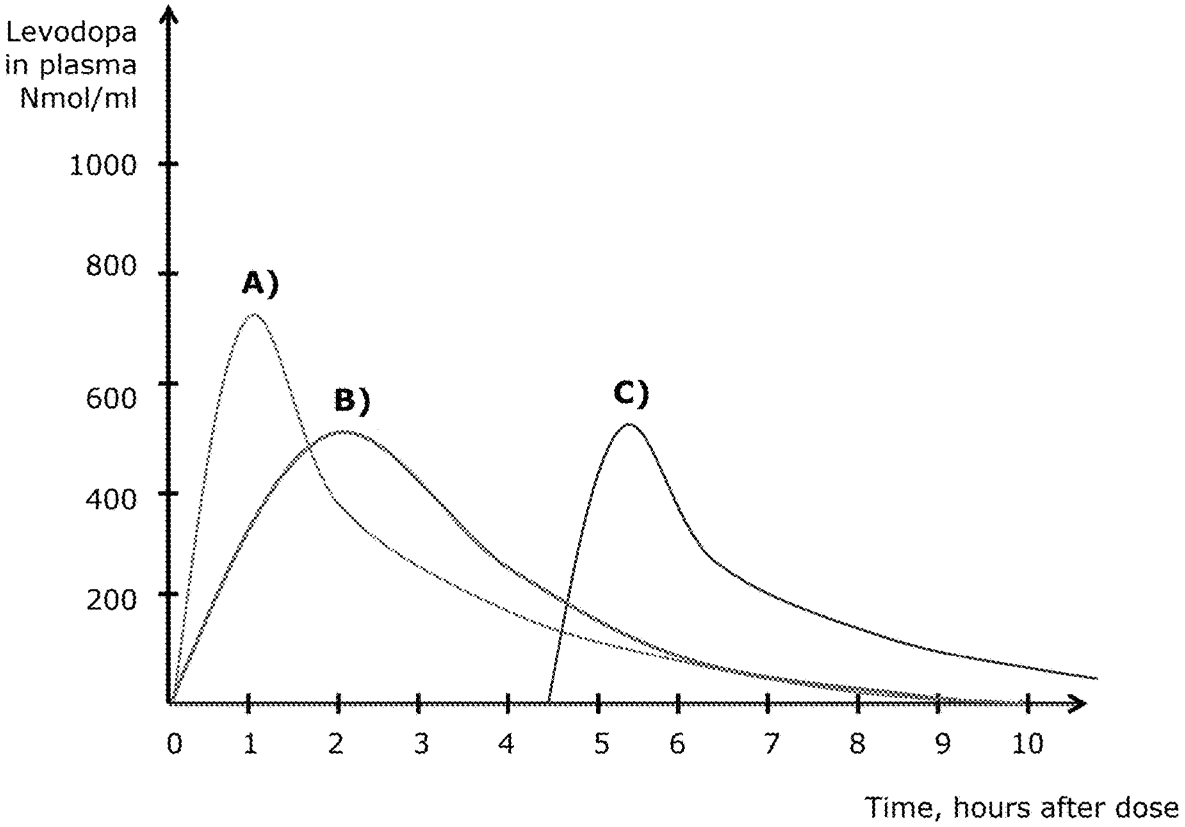
FIG. 1: Pharmacokinetic profiles for levodopa products; A) standard immediate release, B) standard controlled release, and C) proposed delayed pulsatile product.

It is an aspect to provide a pharmaceutical composition that provides for timed pulsatile release of levodopa and a DOPA decarboxylase inhibitor such as carbidopa in the small intestine; preferably separated in time whereby the DOPA decarboxylase inhibitor such as carbidopa is pulse released before levodopa. By ingesting such composition prior to sleep provides a means for treating morning akinesia in patients with e.g. Parkinson's disease.

It is recognized that gastric motility generally is somewhat delayed in patients with Parkinson's disease, hence a lag time release of up to 5 or 6 hours while the composition still is in the small intestine is feasible. Delivering a full dose of levodopa in a burst in the lower part of the small intestine is expected to improve the absorption of levodopa. Bioabsorption in this region is not possible with the current marketed levodopa products, and therefore the new principle provides a unique new opportunity for having over-night levodopa coverage for the Parkinson patient.

L-DOPA or levodopa (L-3,4-dihydroxyphenylalanine) in humans is synthesized from the amino acid L-tyrosine. L-DOPA is the precursor to the neurotransmitters dopamine, noradrenaline and adrenaline and mediates neurotrophic factor release by the brain and CNS. L-DOPA is sold as a psychoactive drug with the INN levodopa; trade names include Sinemet, Pharmacopa, Atamet, Stalevo, Madopar, and Prolopa. It is used in the clinical treatment of Parkinson's disease and dopamine-responsive dystonia.

L-DOPA crosses the blood-brain barrier where it is converted into dopamine by aromatic L-amino acid decarboxylase (DOPA decarboxylase). Since L-DOPA is also converted into dopamine from within the peripheral nervous system, causing excessive peripheral dopamine signaling and adverse effects, it is standard clinical practice to co-administer a peripheral DOPA decarboxylase inhibitor (DDCI). Combined therapy potentiates the central effects of L-DOPA by decreasing the dose-dependency 4-5 fold.

DOPA decarboxylase inhibitors includes carbidopa, benserazide, methyldopa and DFMD (α-Difluoromethyl-DOPA).

Medicines containing carbidopa, either alone or in combination with L-DOPA, are branded as Lodosyn (Aton Pharma), Sinemet (Merck Sharp & Dohme Limited), Pharmacopa (Jazz Pharmaceuticals), Atamet (UCB), Stalevo (Orion Corporation), parcopa, or with a benserazide (combination medicines are branded Madopar or Prolopa).

Medicines containing benserazide either alone or in combination with L-DOPA are branded as Madopar, Prolopa, Modopar, Madopark, Neodopasol, EC-Doparyl, etc. Medicines containing methyldopa are branded as Aldomet, Aldoril, Dopamet, Dopegyt, etc.

Pulsatile drug delivery is defined as the rapid and transient release of certain amount of molecules within a short time period immediately after a predetermined off-released period, i.e., lag time.

Pulsatile drug delivery systems (PDDS) deliver the drug at the right time, at the right site of action and in the right amount, and the drug is released rapidly and completely as a pulse (or burst) after a lag time. These products follow the sigmoid release profile characterized by a time period. Such a release pattern is known as pulsatile release. These systems are beneficial for the drug with chrono-pharmacological behavior, where nocturnal dosing is required, and for drugs that show first pass effect. Potential disadvantages include low drug loading capacity and multiple manufacturing steps.

Lag time is defined as the time between when a dosage form is placed into an aqueous environment and the time at which the active pharmaceutical ingredient begins to get released from the dosage form.

Pulsatile drug delivery systems may be broadly classified in three categories:

1) Time controlled pulsatile release systems (delivery systems containing erodible coating layer)
   a. Bulk-eroding systems. Bulk erosion means that the ingress of water is faster than the rate of degradation. In this case, degradation take places throughout the polymer sample and proceeded until a critical molecular weight is reached. At this point, degradation products become smaller enough to be solubilised and the structure starts to become significantly more porous and hydrated. Hence there is a time lag before the drug can be released, corresponding to the time required for critical molecular weight to be reached.
   b. Surface-eroding systems. In this type of system, the reservoir device is coated with soluble or erodible layer, which dissolves with time and releases the drug after a specified lag period. When this system comes in contact with aqueous medium the coat emulsifies or erodes after the lag-time. It is independent of the gastrointestinal motility, pH, enzyme and gastric residence. The lag time and onset of action are controlled by thickness and the viscosity grade of the polymer used. Examples include delivery systems with rupturable coating layer and capsule-shaped system with release controlling plug.
      a. The coating can be spray coated (e.g. rupture film coatings or erodible film coatings) or compression coated.
2) Stimuli-induced pulsatile release system. Stimuli based drug delivery systems release the drug in response to stimuli that are induced by the biological environment, such as changes in temperature (thermo-responsive pulsatile release) and chemical stimuli such as pH, enzymes or other chemicals (chemical stimuli-induced pulsatile release).
3) Externally regulated pulsatile release system. These include electrically responsive delivery systems (prepared from polyelectrolytes and thus pH-responsive as well as electro responsive); ultrasonically stimulated; and magnetically induced pulsatile release.

Provided herewith is a pulsatile drug delivery system providing for the timed pulsatile release of levodopa and a DOPA decarboxylase inhibitor. In one embodiment the pulsatile drug delivery system is a pharmaceutical composition for timed pulsatile release of levodopa and a DOPA decarboxylase inhibitor.

A pharmaceutical composition and a pulsatile release pharmaceutical composition may be used interchangeably herein.

In one aspect there is provided a pulsatile release pharmaceutical composition comprising i) levodopa and a DOPA decarboxylase inhibitor, and
ii) a pulsatile release component providing for a predetermined lag time followed by a pulse release of said levodopa and said DOPA decarboxylase inhibitor.

In one aspect there is provided a pharmaceutical composition comprising, separately or together, i) a first pulsatile release component comprising levodopa, said first pulsatile release component providing for a predetermined lag time followed by a pulse release of levodopa, and
ii) a second pulsatile release component comprising a DOPA decarboxylase inhibitor, said second pulsatile release component providing for a predetermined lag time followed by a pulse release of said DOPA decarboxylase inhibitor.

In one embodiment the lag time of said first pulsatile release component comprising levodopa is longer than the lag time of said second pulsatile release component comprising a DOPA decarboxylase inhibitor.

In one aspect there is provided a pharmaceutical composition comprising, separately or together, i) a first pulsatile release component comprising levodopa, said first pulsatile release component providing for a predetermined lag time followed by a pulse release of levodopa, and
ii) a second pulsatile release component comprising a DOPA decarboxylase inhibitor, said second pulsatile release component providing for a predetermined lag time followed by a pulse release of said DOPA decarboxylase inhibitor, wherein the lag time of said first pulsatile release component comprising levodopa is longer than the lag time of said second pulsatile release component comprising a DOPA decarboxylase inhibitor.

In one embodiment the DOPA decarboxylase inhibitor is selected from the group consisting of carbidopa, benserazide, methyldopa and DFMD (α-Difluoromethyl-DOPA), or a pharmaceutically acceptable derivative thereof.

In one embodiment the DOPA decarboxylase inhibitor is carbidopa, or pharmaceutically acceptable derivative thereof.

In one embodiment the term levodopa comprises also pharmaceutically acceptable derivatives of levodopa.

In one embodiment the term levodopa comprises levodopa pro-drugs. In one embodiment the term levodopa comprises the levodopa pro-drug levodopa methyl ester. In one embodiment the term levodopa comprises the levodopa pro-drug XP21279.

In one embodiment the term levodopa comprises also modified levodopa. In one embodiment the term levodopa comprises also deuterated levodopa (deuterium substituted levodopa).

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

In one embodiment the pharmaceutical composition is a time controlled pulsatile release system, including bulk-eroding systems and surface-eroding systems.

In one embodiment the pharmaceutical composition is a pharmaceutical dosage form.

In one embodiment the pharmaceutical dosage form is a multiparticulate dosage form (multiple unit dosage forms).

Multiparticulates or multiple unit dosage forms are the discrete, small, repetitive units of drug particles which may or possess similar drug release pattern. They can be tailored for pulsatile drug release.

In one embodiment the pharmaceutical dosage form is a multiparticulate dosage form comprising a plurality of particles, each particle providing for timed pulsatile release of levodopa and/or a DOPA decarboxylase inhibitor.

In one embodiment the pharmaceutical dosage form is a multiparticulate dosage form comprising, separately or together, two dosage forms:

i) a first dosage form providing for a predetermined lag time followed by a pulse release of levodopa, and
ii) a second dosage form providing for a predetermined lag time followed by a pulse release of a DOPA decarboxylase inhibitor.

In one embodiment the pharmaceutical dosage form is a multiparticulate dosage form comprising, separately or together, two dosage forms:

i) a first dosage form providing for a predetermined lag time followed by a pulse release of levodopa, and
ii) a second dosage form providing for a predetermined lag time followed by a pulse release of a DOPA decarboxylase inhibitor, wherein the lag time of said first dosage form comprising levodopa is longer than the lag time of said second dosage form comprising a DOPA decarboxylase inhibitor.

In one embodiment the multiparticulate dosage form is packaged in a capsule, a pouch a sachet or a stick pack. In one embodiment the first dosage form comprising levodopa and the second dosage form comprising a DOPA decarboxylase inhibitor are packaged in a capsule, a pouch, a sachet or a stick pack. In one embodiment the capsule is a hard-shelled capsule, such as hard-capsule gelatin.

In one embodiment the multiparticulate dosage form i) comprises 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, 24 to 25, 25 to 26, 26 to 27, 27 to 28, 28 to 29, 29 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 110, 110 to 120, 120 to 130, 130 to 140, 140 to 150, 150 to 160, 160 to 170, 170 to 180, 180 to 190, 190 to 200 first dosage forms comprising levodopa; and
ii) comprises 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, 24 to 25, 25 to 26, 26 to 27, 27 to 28, 28 to 29, 29 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 110, 110 to 120, 120 to 130, 130 to 140, 140 to 150, 150 to 160, 160 to 170, 170 to 180, 180 to 190, 190 to 200 second dosage forms comprising a DOPA decarboxylase inhibitor.

The number of dosage forms in the multiparticulate dosage form is determined by factors such as dosage of active pharmaceutical ingredient and size of dosage form.

In one embodiment the pharmaceutical dosage form; such as the first and the second dosage form, is an oral solid dosage form. In one embodiment the oral solid dosage form is selected from the group consisting of a tablet, a mini-tablet, a micro-tablet, a sphere, a pellet, a granule and a capsule.

In one embodiment the oral solid dosage form comprises a coating. In one embodiment the oral solid dosage form comprises a core with a coating. In one embodiment the core comprises the active pharmaceutical ingredient. In one embodiment the coating does not contain the active pharmaceutical ingredient.

In one embodiment the oral solid dosage form is selected from the group consisting of a coated tablet, a coated mini-tablet, a coated micro-tablet, a coated sphere, a coated pellet, a coated granule and a coated capsule.

In one embodiment the oral solid dosage form comprise a swellable and soluble core.

In one embodiment the coating is a film coating.

In one embodiment the coating is a semi-permeable coating, such as a semi-permeable insoluble film coating. Upon swelling of the core the active pharmaceutical ingredient is released through the semi-permeable film coating.

In one embodiment the coating is an insoluble coating.

In one embodiment the coating is a rupturable coating.

In one embodiment the coating is a rupturable insoluble coating. Upon swelling of the core component the outer coating ruptures and burst releases the contents.

In one embodiment the coating is a soluble or erodible coating.

In one embodiment the oral solid dosage form comprises a soluble core coated with an insoluble film, such as an insoluble semipermeable film.

In one embodiment the pharmaceutical dosage form is a coated mini-tablet. In one embodiment the pharmaceutical dosage form is a tablet, such as a coated tablet. In one embodiment the pharmaceutical dosage form is a tablet comprising coated mini-tablets compressed into a tablet.

In one embodiment the coating is spray coated. In one embodiment the coating is compression coated.

In one embodiment the outer coating comprises a film-forming polymer. In one embodiment the outer coating comprises a water-insoluble polymer. In one embodiment the outer coating further comprises a pore-former, such as a hydrophilic pore former.

Mini-tablets are tablets with a diameter≤3 mm, and represent a new trend in solid dosage form design, which overcomes some therapeutic obstacles such as impaired swallowing and polypharmacy therapy, and also offering some therapeutic benefits such as dose flexibility and combined release patterns.

In one embodiment a mini-tablet is a tablet with a diameter less than or equal to (≤) 3 mm, such as ≤2.5 mm, for example ≤2 mm, such as ≤1.5 mm, for example ≤1 mm. In one embodiment a mini-tablet is a tablet with a diameter of 1 to 1.5 mm, such as 1.5 to 2 mm, for example 2 to 2.5 mm, such as 2.5 to 3 mm. In one embodiment a mini-tablet is a tablet with a diameter of approximately 2 mm.

In one embodiment the pharmaceutical composition provides for a sigmoid release profile of levodopa and of a DOPA decarboxylase inhibitor, preferably shifted in time wherein the lag time of a first pulsatile release of levodopa is longer than the lag time of the second pulsatile release of a DOPA decarboxylase inhibitor.

The lag time for the pulsatile release component is adjusted to release said levodopa and said DOPA decarboxylase inhibitor in the small intestine, such as the lower part of the small intestine.

In one embodiment the lag time for the pulsatile release component comprising levodopa and DOPA decarboxylase inhibitor is between 2 to 8 hours; such as 2 to 3 hours, such as 3 to 4 hours, such as 4 to 5 hours, such as 5 to 6 hours, such as 6 to 7 hours, such as 7 to 8 hours.

The lag time for the first pulsatile release component comprising levodopa, and for the second pulsatile release component comprising a DOPA decarboxylase inhibitor is preferably adjusted to release the active pharmaceutical ingredients in the small intestine, such as the lower part of the small intestine. Preferably, the DOPA decarboxylase inhibitor is released before the levodopa is released in the small intestine, such as the lower part of the small intestine.

In one embodiment the lag time for the first pulsatile release component comprising levodopa is between 2 to 8 hours; such as 2 to 3 hours, such as 3 to 4 hours, such as 4 to 5 hours, such as 5 to 6 hours, such as 6 to 7 hours, such as 7 to 8 hours.

In one embodiment thee lag time for the first pulsatile release component comprising levodopa is 3 to 6 hours, such as 4 to 6 hours, such as 3 to 5 hours.

In one embodiment the lag time for the first pulsatile release component comprising levodopa is at least 2 hours, such as at least 3 hours, such as at least 4 hours.

In one embodiment the lag time for the second pulsatile release component comprising a DOPA decarboxylase inhibitor is between 2 to 8 hours; such as 2 to 3 hours, such as 3 to 4 hours, such as 4 to 5 hours, such as 5 to 6 hours, such as 6 to 7 hours, such as 7 to 8 hours.

In one embodiment thee lag time for the second pulsatile release component comprising a DOPA decarboxylase inhibitor is 3 to 6 hours, such as 4 to 6 hours, such as 3 to 5 hours.

In one embodiment the lag time for the second pulsatile release component comprising a DOPA decarboxylase inhibitor is at least 2 hours, such as at least 3 hours, such as at least 4 hours.

In one embodiment the lag time of the first dosage form comprising levodopa and the second dosage form comprising a DOPA decarboxylase inhibitor is shifted in time, whereby the lag time of the first dosage form comprising levodopa is longest.

In one embodiment the lag time of the first dosage form comprising levodopa is longer than the lag time of the second dosage form comprising a DOPA decarboxylase inhibitor, such that the DOPA decarboxylase inhibitor is release before levodopa is released.

In one embodiment the lag time of the first dosage form comprising levodopa is 5 minutes to 90 minutes longer than the lag time of the second dosage form comprising a DOPA decarboxylase inhibitor; such as 5 to 10 minutes, such as 10 to 15 minutes, such as 15 to 20 minutes, such as 20 to 25 minutes, such as 25 to 30 minutes, such as 30 to 35 minutes, such as 35 to 40 minutes, such as 40 to 45 minutes, such as 45 to 50 minutes, such as 50 to 55 minutes, such as 55 to 60 minutes, such as 60 to 65 minutes, such as 65 to 70 minutes, such as 70 to 75 minutes, such as 75 to 80 minutes, such as 80 to 85 minutes, such as 85 to 90 minutes longer than the lag time of the second dosage form comprising a DOPA decarboxylase inhibitor.

In one embodiment the lag time of the first dosage form comprising levodopa is 90 minutes to 240 minutes longer than the lag time of the second dosage form comprising a DOPA decarboxylase inhibitor; such as 90 to 100 minutes, such as 100 to 110 minutes, such as 110 to 120 minutes, such as 120 to 130 minutes, such as 130 to 140 minutes, such as 140 to 150 minutes, such as 150 to 160 minutes, such as 160 to 170 minutes, such as 170 to 180 minutes, such as 180 to 200 minutes, such as 200 to 220 minutes, such as 220 to 240 minutes longer than the lag time of the second dosage form comprising a DOPA decarboxylase inhibitor.

In one embodiment the lag time of the first dosage form comprising levodopa is at least 5 minutes longer than the lag time of the second dosage form comprising a DOPA decarboxylase inhibitor, such as at least 10 minutes longer, such as at least 15 minutes longer, such as at least 20 minutes longer, such as at least 25 minutes longer, such as at least 30 minutes longer, such as at least 35 minutes, such as at least 40 minutes longer, such as at least 45 minutes, such as at least 50 minutes longer, such as at least 55 minutes, such as at least 60 minutes longer than the lag time of the second dosage form comprising a DOPA decarboxylase inhibitor.

In one embodiment the lag time of the first dosage form comprising levodopa is approximately 10 minutes longer, such as approximately 15 minutes longer, such as approximately 20 minutes longer, such as approximately 25 minutes longer, such as approximately 30 minutes longer, such as approximately 35 minutes, such as approximately 40 minutes longer, such as approximately 45 minutes, such as approximately 50 minutes longer, such as approximately 55 minutes, such as approximately 60 minutes longer than the lag time of the second dosage form comprising a DOPA decarboxylase inhibitor.

After the lag time the active pharmaceutical ingredient is released from the pharmaceutical composition or dosage form.

In one embodiment the first dosage form comprising levodopa is released before the second dosage form comprising a DOPA decarboxylase inhibitor.

In one embodiment the first dosage form comprising levodopa is released 5 to 10 minutes before, such as 10 to 15 minutes, such as 15 to 20 minutes, such as 20 to 25 minutes, such as 25 to 30 minutes, such as 30 to 35 minutes, such as 35 to 40 minutes, such as 40 to 45 minutes, such as 45 to 50 minutes, such as 50 to 55 minutes, such as 55 to 60 minutes, such as 60 to 65 minutes, such as 65 to 70 minutes, such as 70 to 75 minutes, such as 75 to 80 minutes, such as 80 to 85 minutes, such as 85 to 90 minutes before release of the second dosage form comprising a DOPA decarboxylase inhibitor.

In one embodiment the pharmaceutical composition releases 70 to 100% of the drug load measured at 2 to 5 hours after the lag phase, i.e. releases 70 to 100% of the levodopa and/or the DOPA decarboxylase inhibitor measured at 2 to 5 hours.

In one embodiment the pharmaceutical composition releases 70 to 100% of the drug load measured at 2 to 5 hours, such as releases 70 to 75%, such as 75 to 80%, such as 80 to 85%, such as 85 to 90%, such as 90 to 95%, such as 95 to 100% of the drug load measured at 2 to 5 hours.

In one embodiment the pharmaceutical composition releases up to 100% of the drug load within 2 hours after the lag phase. In one embodiment the pharmaceutical composition releases 70%, such as 80%, such as 90%, such as 100% of the drug load within 2 hours after the lag phase. In one embodiment the pharmaceutical composition releases 70%, such as 80%, such as 90%, such as 100% of the drug load within 2 to 5 hours after the lag phase, such as within 2 hours, such as within 3 hours, such as within 4 hours, such as within 5 hours.

Coated Tablets

In one embodiment the pharmaceutical dosage form comprises one or more coated tablets comprising levodopa and a DOPA decarboxylase inhibitor providing for a predetermined lag time followed by a pulse release of said levodopa and said DOPA decarboxylase inhibitor.

In one embodiment the pharmaceutical dosage form is a multiparticulate dosage form comprising, separately or together, i) coated tablets providing for a predetermined lag time followed by a pulse release of levodopa, and
ii) coated tablets providing for a predetermined lag time followed by a pulse release of a DOPA decarboxylase inhibitor.

In one embodiment the lag time of said coated tablets comprising levodopa is longer than the lag time of said coated tablets comprising a DOPA decarboxylase inhibitor.

In one embodiment the coated tablets comprise a tablet core comprising the active pharmaceutical ingredient and an outer coating.

Coated tablets comprise both coated tablets and coated mini-tablets. In one embodiment the coated tablets are coated tablets. In one embodiment the coated tablets are coated mini-tablets.

In one embodiment the coated tablets comprise a swellable and soluble mini-tablet core.

In one embodiment the coated tablets comprise a semi-permeable film coating. Upon swelling of the core the active pharmaceutical ingredient is released through the semipermeable film.

In one embodiment the coated tablets are coated mini-tablets comprising a semi-permeable film coating. Upon swelling of the mini-tablet core the active pharmaceutical ingredient is released through the semipermeable film.

In one embodiment the coated tablets comprise a rupturable insoluble coating. Upon swelling of the core component the outer coating ruptures and burst releases the contents.

In one embodiment coated mini-tablets comprising levodopa comprise a swellable and soluble mini-tablet core comprising levodopa and an outer semipermeable film coating.

In one embodiment coated mini-tablets comprising a DOPA decarboxylase inhibitor comprise a swellable and soluble mini-tablet core comprising a DOPA decarboxylase inhibitor and an outer semipermeable film coating.

In one embodiment coated tablets comprising levodopa comprise a swellable and soluble tablet core comprising levodopa and a rupturable insoluble coating.

In one embodiment coated tablets comprising a DOPA decarboxylase inhibitor comprise a swellable and soluble tablet core comprising a DOPA decarboxylase inhibitor and a rupturable insoluble coating.

In one embodiment the tablet core comprising levodopa comprises or consists of:

levodopa
a superdisintegrant,
one or more excipients, and
optionally an anti-adherent.

In one embodiment the tablet core comprises 25 to 75% w/w levodopa, such as 25 to 30%, such as 30 to 35%, such as 35 to 40%, such as 40 to 45%, such as 45 to 50%, such as 50 to 55%, such as 60 to 65%, such as 65 to 70%, such as 70 to 75% w/w levodopa.

In one embodiment the mini-tablet core comprises 1 to 5 mg levodopa, such as 1 to 1.25 mg, such as 1.25 to 1.5 mg, such as 1.5 to 1.75 mg, such as 1.75 to 2 mg, such as 2 to 2.25 mg, such as 2.25 to 2.5 mg, such as 2.5 to 2.75 mg, such as 2.75 to 3 mg, such as 3 to 3.25 mg, such as 3.25 to 3.5 mg, such as 3.5 to 3.75 mg, such as 3.75 to 4 mg, such as 4 to 4.25 mg, such as 4.25 to 4.5 mg, such as 4.5 to 4.75 mg, such as 4.75 to 5 mg levodopa. In one embodiment the mini-tablet core comprises 2.5 to 3.5 mg levodopa. In one embodiment the mini-tablet core comprises at least 2, such as at least 2.5 mg levodopa.

In one embodiment the tablet core comprising a DOPA decarboxylase inhibitor comprises or consists of:

a DOPA decarboxylase inhibitor,
a superdisintegrant,
one or more excipients, and
optionally an anti-adherent.

In one embodiment the tablet core comprises 25 to 75% w/w DOPA decarboxylase inhibitor, such as 25 to 30%, such as 30 to 35%, such as 35 to 40%, such as 40 to 45%, such as 45 to 50%, such as 50 to 55%, such as 60 to 65%, such as 65 to 70%, such as 70 to 75% w/w DOPA decarboxylase inhibitor.

A superdisintegrant is an agent used in pharmaceutical preparation of tablets, which causes them to disintegrate and release their medicinal substances on contact with moisture.

In one embodiment the tablet core comprises 15 to 50% w/w superdisintegrant, such as 15 to 20%, such as 20 to 25%, such as 25 to 30%, such as 30 to 35%, such as 35 to 40%, such as 40 to 45%, such as 45 to 50% w/w superdisintegrant. In one embodiment the tablet core comprises at least 20% w/w superdisintegrant, such as at least 25%, such as at least 30% w/w superdisintegrant. In one embodiment the tablet core comprises at approx. 30% w/w superdisintegrant.

In one embodiment the superdisintegrant is selected from Crosslinked starch, Crosslinked Cellulose, Crosslinked PVP (polyvinylpyrrolidone), Crosslinked alginic acid, Soy polysaccharides, Calcium silicate, Gellan gum and Xanthan gum.

In one embodiment the tablet core comprises one or more superdisintegrants selected from the group consisting of sodium starch glycolate (sodium carboxymethyl starch), croscarmellose sodium, crospovidone, crospovidone XL, crospovidone CL and low-substituted hydroxypropylcellulose (L-HPC). In one embodiment the superdisintegrant is sodium starch glycolate.

An excipient is a pharmacologically inactive (or chemically inactive) substance formulated with the active pharmaceutical ingredient of a medication. Excipients are commonly used to bulk up formulations that contain active pharmaceutical ingredients (thus often referred to as "bulking agents," "fillers," or "diluents") to allow convenient and accurate dispensation of a drug substance when producing a dosage form.

In one embodiment the tablet core comprises 10 to 50% w/w excipients, such as 10 to 15%, such as 15 to 20%, such as 20 to 25%, such as 25 to 30%, such as 30 to 35%, such as 35 to 40%, such as 40 to 45%, such as 45 to 50% w/w excipients.

In one embodiment said excipients act as binder, filler, solid carrier, diluent, flavouring agent, solubilizer, lubricant, glidant, suspending agent, preservative, anti-adherent, wetting agent, disintegrating agent or sorbent or combinations thereof.

In one embodiment the tablet core comprises one or more fillers, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment the tablet core comprises one or more binders, such as a binder selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroxyethyl cellulose, hydroxyethylmethyl cellulose, hydroxypropyl cellulose, hydroxypropyl starch, hydroxypropylmethylcellulose (HPMC or hypromellose), methylcellulose, microcrystalline cellulose (MCC), poloxamer, polydextrose, polyethylene oxide, povidone, sodium alginate, sucrose, starch, pregelatinized starch and maltodextrin.

In one embodiment the tablet core comprises one or more wet binders. In one embodiment the mini-tablet core comprises one or more wet binders selected from the group consisting of pregelatinized starch, HPMC, methylcellulose and gelatin.

In one embodiment the tablet core comprises 5 to 25% w/w binder, such as 5 to 7.5%, such as 7.5 to 10%, such as 10 to 12.5%, such as 12.5 to 15%, such as 15 to 17.5%, such as 17.5 to 20%, such as 20 to 22.5%, such as 22.5 to 25% w/w binder.

In one embodiment the tablet core comprises 1 to 20% w/w wet binder, such as 1 to 2.5%, such as 2.5 to 5%, such as 5 to 7.5%, such as 7.5 to 10%, such as 10 to 12.5%, such as 12.5 to 15%, such as 15 to 17.5%, such as 17.5 to 20% w/w wet binder.

In one embodiment the mini-tablet core comprises microcrystalline cellulose (MCC) and pregelatinized starch.

In one embodiment the tablet core comprises 5 to 25% w/w microcrystalline cellulose, such as 5 to 7.5%, such as 7.5 to 10%, such as 10 to 12.5%, such as 12.5 to 15%, such as 15 to 17.5%, such as 17.5 to 20%, such as 20 to 22.5%, such as 22.5 to 25% w/w microcrystalline cellulose. In one embodiment the mini-tablet core comprises 10 to 20% w/w microcrystalline cellulose.

In one embodiment the tablet core comprises 1 to 20% w/w pregelatinized starch, such as 1 to 2.5%, such as 2.5 to 5%, such as 5 to 7.5%, such as 7.5 to 10%, such as 10 to 12.5%, such as 12.5 to 15%, such as 15 to 17.5%, such as 17.5 to 20% w/w pregelatinized starch. In one embodiment the mini-tablet core comprises 5 to 15% w/w such as 5 to 10% w/w pregelatinized starch.

In one embodiment the tablet core comprises an anti-adherent, such as comprises 0.25 to 0.50% w/w anti-adherent, such as 0.50 to 0.75%, such as 0.75 to 1.0%, such as 1.0 to 1.25, such as 1.25 to 1.50, such as 1.50 to 1.75%, such as 1.75 to 2.0% w/w anti-adherent.

In one embodiment the anti-adherent is selected from the group consisting of magnesium stearate, calcium stearate, zinc stearate, glyceryl monostearate, hydrogenated castor oil, hydrogenated vegetable oil, medium chain glycerides, palmitic acid, poloxamers, polyethylene glycols, stearic acid and talc. In one embodiment the anti-adherent is magnesium stearate.

In one embodiment the tablet core comprising levodopa comprises or consists of:

25 to 75% w/w levodopa; such as 25 to 30%, such as 30 to 35%, such as 35 to 40%, such as 40 to 45%, such as 45 to 50%, such as 50 to 55%, such as 60 to 65%, such as 65 to 70%, such as 70 to 75% w/w levodopa, 15 to 50% w/w superdisintegrant; such as 15 to 20%, such as 20 to 25%, such as 25 to 30%, such as 30 to 35%, such as 35 to 40%, such as 40 to 45%, such as 45 to 50% w/w superdisintegrant, 10 to 50% w/w excipients; such as 10 to 15%, such as 15 to 20%, such as 20 to 25%, such as 25 to 30%, such as 30 to 35%, such as 35 to 40%, such as 40 to 45%, such as 45 to 50% w/w excipients, and 0 to 2% w/w anti-adherent; such as 0.25 to 0.50% w/w anti-adherent, such as 0.50 to 0.75%, such as 0.75 to 1.0%, such as 1.0 to 1.25, such as 1.25 to 1.50, such as 1.50 to 1.75%, such as 1.75 to 2.0% w/w anti-adherent.

In one embodiment the tablet core comprising levodopa comprises or consists of:

40 to 60% w/w levodopa, 20 to 40% w/w superdisintegrant, 10 to 30% w/w excipients, and 0.5 to 1.5% w/w anti-adherent.

In one embodiment the tablet core comprising levodopa comprises or consists of:

40 to 60% w/w, such as 45 to 55% w/w levodopa, 20 to 40% w/w, such as 25 to 35% w/w sodium starch glycolate, 5 to 25% w/w, such as 10 to 20% w/w microcrystalline cellulose, 1 to 20% w/w, such as 5 to 10% w/w pregelatinized starch, and 0.5 to 1.5% w/w, such as 1% w/w Mg stearate.

In one embodiment the tablet core comprising DOPA decarboxylase inhibitor comprises or consists of:

25 to 75% w/w DOPA decarboxylase inhibitor; such as 25 to 30%, such as 30 to 35%, such as 35 to 40%, such as 40 to 45%, such as 45 to 50%, such as 50 to 55%, such as 60 to 65%, such as 65 to 70%, such as 70 to 75% w/w DOPA decarboxylase inhibitor, 15 to 50% w/w superdisintegrant; such as 15 to 20%, such as 20 to 25%, such as 25 to 30%, such as 30 to 35%, such as 35 to 40%, such as 40 to 45%, such as 45 to 50% w/w superdisintegrant, 10 to 50% w/w excipients; such as 10 to 15%, such as 15 to 20%, such as 20 to 25%, such as 25 to 30%, such as 30 to 35%, such as 35 to 40%, such as 40 to 45%, such as 45 to 50% w/w excipients, and 0 to 2% w/w anti-adherent; such as 0.25 to 0.50% w/w anti-adherent, such as 0.50 to 0.75%, such as 0.75 to 1.0%, such as 1.0 to 1.25, such as 1.25 to 1.50, such as 1.50 to 1.75%, such as 1.75 to 2.0% w/w anti-adherent.

In one embodiment the tablet core comprises carbidopa.

In one embodiment the coated tablet is manufactured by granulation, compression and subsequent film coating.

In one embodiment coated mini-tablets are compressed to form a tablet.

In one embodiment coated mini-tablets are packaged in a capsule, a pouch a sachet or a stick pack.

Coating

It is envisioned that the outer coating is applied to increase the weight of the tablet to a certain extent, whereby release of substances is delayed. Weight increase or weight gain as defined herein is increased relative to the tablet core weight.

In one embodiment an outer coating is applied to increase the weight of a mini-tablet core by 10 to 40% w/w, such as 10 to 12.5%, such as 12.5 to 15%, such as 15 to 17.5%, such as 17.5 to 20%, such as 20 to 22.5%, such as 22.5 to 25%, such as 25 to 27.5%, such as 27.5 to 30%, such as 30 to 32.5%, such as 32.5 to 35%, such as 35 to 37.5%, such as 37.5 to 40% w/w. In one embodiment this applies to mini-tablet cores comprising levodopa and mini-tablet cores comprising a DOPA decarboxylase inhibitor.

In one embodiment an outer coating is applied to increase the weight of a mini-tablet core by 17.5% to 25% w/w, such as 20 to 25% w/w.

In one embodiment an outer coating is applied to increase the weight of a mini-tablet core by at least 15% w/w, such as at least 17.5%, such as at least 20%, such as at least 22.5%, such as at least 25% w/w.

In one embodiment the outer coating is applied to increase the weight of a mini-tablet core by approximately 15% w/w, such as approximately 17.5%, such as approximately 20%, such as approximately 22.5%, such as approximately 25%, such as approximately 27.5%, such as approximately 30% w/w.

In one embodiment an outer coating is applied to increase the weight of a tablet core (not mini-tablet) by 1 to 20% w/w, such as 1 to 2.5%, such as 2.5 to 5%, such as 5 to 7.5%, such as 7.5 to 10%, such as 10 to 12.5%, such as 12.5 to 15%, such as 15 to 17.5%, such as 17.5 to 20% w/w. In one embodiment this applies to tablet cores comprising levodopa and tablet cores comprising a DOPA decarboxylase inhibitor.

In one embodiment the outer coating is applied to the tablet core comprising levodopa to achieve the desired lag time defined herein elsewhere.

In one embodiment the outer coating is applied to the tablet core comprising a DOPA decarboxylase inhibitor to achieve the desired lag time defined herein elsewhere.

In one embodiment the weight increase of the outer coating of the tablet core comprising levodopa, and the weight increase of the outer coating of the tablet core comprising a DOPA decarboxylase inhibitor, are adjusted in order to release levodopa before the DOPA decarboxylase inhibitor, as specified herein.

In one embodiment the weight increase of the outer coating of the tablet core comprising levodopa is higher than and the weight increase of the outer coating of the tablet core comprising a DOPA decarboxylase inhibitor.

In one embodiment the weight increase of the outer coating of the tablet core comprising levodopa is 1 to 25 percentage point higher than and the weight increase of the outer coating of the tablet core comprising a DOPA decarboxylase inhibitor, such as 1 to 2 percentage point, such as 2 to 3 percentage point, such as 3 to 4 percentage point, such as 4 to 5 percentage point, such as 5 to 6 percentage point, such as 6 to 7 percentage point, such as 7 to 8 percentage point, such as 8 to 9 percentage point, such as 9 to 10 percentage point, such as 10 to 11 percentage point, such as 11 to 12 percentage point, such as 12 to 13 percentage point, such as 13 to 14 percentage point, such as 14 to 15 percentage point higher, such as 15 to 16 percentage point, such as 16 to 17 percentage point, such as 17 to 18 percentage point, such as 18 to 19 percentage point, such as 19 to 20 percentage point, such as 20 to 21 percentage point, such as 21 to 22 percentage point, such as 22 to 23 percentage point, such as 23 to 24 percentage point, such as 24 to 25 percentage point higher.

In one embodiment the coating is an insoluble and rupturable film.

In one embodiment the coating is an insoluble and semipermeable film.

In one embodiment the coating is a semipermeable film.

In one embodiment the coating comprises a film-forming polymer.

In one embodiment the coating comprises a water-insoluble polymer.

In one embodiment the coating comprises one or more of ethylcellulose, hydroxypropyl cellulose, cellulose acetate, acrylic polymers, enteric polymers, hypromellose acetate succinate, shellac, vax and ethylcellulose dispersions.

In one embodiment the coating comprises ethylcellulose.

In one embodiment the coating further comprises a pore-former, such as a hydrophilic pore former. In one embodiment the pore-former is selected from the group consisting of polyvinyl alcohol (PVA), hydroxypropyl methylcellulose (HPMC), polyvinylpyrrolidone (PVP) and polyethylene glycol (PEG).

In one embodiment the coating comprises a water-insoluble polymer and a hydrophilic pore former.

In one embodiment the coating comprises ethylcellulose and a pore-former, such as a pore-former selected from PVA, HPMC, PVP and PEG. In one embodiment the outer coating comprises ethylcellulose and PVA. In one embodiment the outer coating comprises ethylcellulose and HPMC.

In one embodiment the coating comprises 5 to 40% w/w pore-former, such as 5 to 10% w/w, such as 10 to 15% w/w, such as 15 to 20% w/w, such as 20 to 25% w/w, such as 25 to 30% w/w, such as 30 to 35% w/w, such as 35 to 40% w/w pore-former. In one embodiment the outer coating comprises 10 to 30%, such as 15 to 25% w/w pore-former.

In one embodiment the ratio in the coating of the film-forming polymer (or water-insoluble polymer) and hydrophilic pore-former is approx. 10/90, 15/85, 20/80, 25/75 or 30/70.

In one embodiment the coating comprises approx. 80% w/w ethylcellulose and approx. 20% w/w HPMC. In one embodiment the outer coating comprises approx. 80% w/w ethylcellulose and approx. 20% w/w PVA.

Administration and Dosage

The pharmaceutical composition disclosed herein is preferably administered to individuals in need of treatment in pharmaceutically effective doses. A therapeutically effective amount of a compound or active pharmaceutical ingredient is an amount sufficient to cure, prevent, reduce the risk of, alleviate or partially arrest the clinical manifestations of a given disease or movement disorder and its complications. The amount that is effective for a particular therapeutic purpose will depend on the severity and the sort of the movement disorder as well as on the weight and general state of the subject.

The pharmaceutical composition according to the present disclosure may be administered one or several times per day such as 1 to 4 times per day, such as 1 to 3 times per day, such as 1 to 2 times per day, such as 2 to 4 times per day, such as 2 to 3 times per day. In a particular embodiment, the composition is administered once a day, such as twice per day, for example 3 times per day, such as 4 times per day.

Administration may occur for a limited time or administration may be chronic such as chronic from the onset of diagnosis, such as throughout the lifetime of the individual or as long as the individual will benefit therefrom i.e. when a movement disorder is present or while having an increased risk of developing a movement disorder.

In one embodiment, the pharmaceutical composition is to be administered as long as a movement disorder is present or as long as an increased risk of developing a movement disorder is present.

The concentration of each of the active pharmaceutical ingredients in the present pharmaceutical composition; namely i) levodopa and ii) a DOPA decarboxylase inhibitor is optimized to achieve an appropriate dosage of each active pharmaceutical ingredient.

In one embodiment the pharmaceutical composition comprises levodopa in an amount of 1 mg to 1000 mg per dosage; such as about 1, 2, 3, 4, 5, 6, 7, 8, 9, 10, 15, 20, 25, 50, 100, 150, 200, 250, 300, 400, 500, 600, 700, 800, 900 or 1000 mg of levodopa per dosage, wherein said dosage may consist of one or multiple dosage forms comprising said amount of levodopa.

Likewise the pharmaceutical composition in one embodiment further comprises a DOPA decarboxylase inhibitor in an amount of 1 to 250 mg per dosage;

such as about 1, 2, 3, 4, 5, 6, 7, 8, 9, 10, 15, 20, 25, 50, 75, 100, 125, 150, 175, 200 or 250 mg DOPA decarboxylase inhibitor per dosage, wherein said dosage may consist of one or multiple dosage forms comprising said amount of a DOPA decarboxylase inhibitor.

In a particular embodiment the amount of levodopa in the pharmaceutical composition is about 100 mg and the amount of a DOPA decarboxylase inhibitor, such as carbidopa, is about 25 mg.

In one embodiment the pharmaceutical composition is a multiparticulate dosage form comprising i) a first dosage form comprising about 100 mg levodopa in 10 to 50 mini-tablets, such as 20 to 40 mini-tablets, such as in about 33 mini-tablets, and
ii) a second dosage form comprising about 25 mg of a DOPA decarboxylase inhibitor such as carbidopa in 5 to 15 mini-tablets, such as in about 10 mini-tablets.

Treatment of Morning Akinesia

Oral levodopa typically provides robust dependable relief of symptoms when it is first started. However, after taking the medicine for many months or years, most patients with Parkinson's disease begin to develop a fluctuating response to levodopa.

Fluctuating responses are divided into "ON" time, when the medication is working well and controlling Parkinson's symptoms, and "OFF" time when the medication fails or is delayed in working and Parkinson's disease symptoms are poorly controlled. Morning akinesia is one form of "OFF" episodes. Symptoms of morning akinesia include tremor, slowness, muscle stiffness, freezing and falls, and difficulty in moving and walking in the morning.

It is an aspect to provide a pulsatile release pharmaceutical composition as defined herein for use in the treatment of morning akinesia in a patient with Parkinson's disease.

It is an aspect to provide a pulsatile release pharmaceutical composition comprising i) levodopa and a DOPA decarboxylase inhibitor, and
ii) a pulsatile release component providing for a predetermined lag time followed by a pulse release of said levodopa and said DOPA decarboxylase inhibitor, for use in the treatment of morning akinesia in a patient with Parkinson's disease.

It is an aspect to provide a pharmaceutical composition comprising, separately or together, i) a first pulsatile release component comprising levodopa, said first pulsatile release component providing for a predetermined lag time followed by a pulse release of levodopa, and
ii) a second pulsatile release component comprising a DOPA decarboxylase inhibitor, said second pulsatile release component providing for a predetermined lag time followed by a pulse release of said DOPA decarboxylase inhibitor, wherein optionally the lag time of said first pulsatile release component comprising levodopa is longer than the lag time of said second pulsatile release component comprising a DOPA decarboxylase inhibitor, for use in the treatment of morning akinesia in a patient with Parkinson's disease.

It is an aspect to provide use of a pharmaceutical composition comprising, separately or together, i) a first pulsatile release component comprising levodopa, said first pulsatile release component providing for a predetermined lag time followed by a pulse release of levodopa, and
ii) a second pulsatile release component comprising a DOPA decarboxylase inhibitor, said second pulsatile release component providing for a predetermined lag time followed by a pulse release of said DOPA decarboxylase inhibitor, wherein optionally the lag time of said first pulsatile release component comprising levodopa is longer than the lag time of said second pulsatile release component comprising a DOPA decarboxylase inhibitor, for the manufacture of a medicament for the treatment of morning akinesia in a patient with Parkinson's disease.

In one aspect there is provided a method of treating morning akinesia in a patient with Parkinson's disease, said method comprising administering a pharmaceutical composition comprising, separately or together, i) a first pulsatile release component comprising levodopa, said first pulsatile release component providing for a predetermined lag time followed by a pulse release of levodopa, and
ii) a second pulsatile release component comprising a DOPA decarboxylase inhibitor, said second pulsatile release component providing for a predetermined lag time followed by a pulse release of said DOPA decarboxylase inhibitor, wherein optionally the lag time of said first pulsatile release component comprising levodopa is longer than the lag time of said second pulsatile release component comprising a DOPA decarboxylase inhibitor.

Also provided is a pharmaceutical composition as defined herein for use in a method of a) improving the night time sleeping pattern in a patient with Parkinson's disease; b) reducing sleep disorders involved in triggering early morning OFF periods; c) providing over-night levodopa coverage for a patient with Parkinson's disease; d) reducing OFF-time in a patient with Parkinson's disease; e) reducing dopaminergic nocturnal decline; and/or f) increase ON-time in a patient with Parkinson's disease.

Also provided is a pharmaceutical composition as defined herein for use in a method of reducing motor symptoms and nonmotor symptoms associated with morning akinesia in a patient with Parkinson's disease.

The predominant nonmotor symptoms associated with morning akinesia are urgency of urination, anxiety, dribbling of saliva, pain, low mood, limb paresthesia, and dizziness.

Other symptoms that have been recently associated with morning akinesia include post-prandial bloating, abdominal discomfort, early satiety, nausea, vomiting, weight loss, and malnutrition.

The terms "treatment" and "treating" as used herein refer to the management and care of a patient for the purpose of combating a condition, disease or disorder. The term is intended to include the full spectrum of treatments for a given condition from which the patient is suffering, such as administration of the composition for the purpose of: alleviating or relieving symptoms or complications; and/or preventing the condition, disease or disorder, wherein "preventing" is to be understood to refer to the management and care of a patient for the purpose of hindering the development of the condition, disease or disorder, and includes the administration of the composition to prevent or reduce the risk of the onset of symptoms or complications. The patient to be treated is preferably a mammal, in particular a human being.

The terms "Parkinson's disease," "Parkinson's" and "PD" refer to a neurological syndrome characterized by a dopamine deficiency, resulting from degenerative, vascular, or inflammatory changes in the basal ganglia of the substantia nigra. This term also refers to a syndrome which resembles Parkinson's disease, but which may or may not be caused by Parkinson's disease, such as Parkinsonian-like side effects caused by certain antipsychotic drugs.

In one embodiment said composition is administered in a therapeutically effective amount. A therapeutically effective amount as used herein refers to an amount sufficient to cure, alleviate, prevent, reduce the risk of, or partially arrest the clinical manifestations of a given disease or disorder and its complications, specifically morning akinesia in a patient with Parkinson's disease.

In one embodiment said pharmaceutical composition is administered prior to sleep.

In one embodiment said pharmaceutical composition is administered once daily prior to sleep.

In one embodiment said pharmaceutical composition is administered before bedtime.

In one embodiment said pharmaceutical composition is administered once daily before bedtime.

In one embodiment said pharmaceutical composition is administered 4 to 0 hours prior to sleep, such as 4 hours to 3½ hours, such as 3½ hours to 3 hours, such as 3 hours to 2½ hours, such as 2½ hours to 2 hours, such as 2 hours to 1½ hours, such as 1½ hours to 1 hour, such as 1 hour to 45 minutes, such as 45 minutes to 30 minutes, such as 30 minutes to 20 minutes, such as 20 minutes to 15 minutes, such as 15 minutes to 10 minutes, such as 10 minutes to 5 minutes, such as 5 minutes to 1 minute, such as 1 minute to 0 minutes prior to sleep.

In one embodiment said pharmaceutical composition is administered 4 to 0 hours before bedtime, such as 4 hours to 3½ hours, such as 3½ hours to 3 hours, such as 3 hours to 2½ hours, such as 2½ hours to 2 hours, such as 2 hours to 1½ hours, such as 1½ hours to 1 hour, such as 1 hour to 45 minutes, such as 45 minutes to 30minutes, such as 30 minutes to 20 minutes, such as 20 minutes to 15 minutes, such as 15 minutes to 10 minutes, such as 10 minutes to 5 minutes, such as 5 minutes to 1 minute, such as 1 minute to 0 minutes before bedtime.

In one embodiment said pharmaceutical composition is administered in combination with an immediate-release levodopa product and/or a controlled-release levodopa-product.

Further Active Pharmaceutical Ingredients

In one embodiment the pharmaceutical composition further comprises, separately or together, one or more further active pharmaceutical ingredients. Such further active pharmaceutical ingredients may be present in the first dosage form comprising levodopa, in the second dosage form comprising a DOPA decarboxylase inhibitor, or in a third dosage form.

A further active pharmaceutical ingredient in one embodiment is selected from the group consisting of dopamine; dopamine receptor agonists such as bromocriptine, pergolide, pramipexole, ropinirole, piribedil, cabergoline, apomorphine, lisuride, and derivatives thereof; catechol-O-methyl transferase (COMT) inhibitors such as for example tolcapone and entacapone; apomorphine such as apomorphine injection; NMDA antagonists such as amatidine (Symmetrel); MAO-B inhibitors such as selegiline and rasagiline; serotonin receptor modulators; kappa opioid receptors agonists such as TRK-820 ((E)-N-[17-cyclopropylmethyl)-4, 5α-epoxy-3, 14-dihydroxymorphinan-6β-yl]-3-(furan-3-yl)-N-methylprop-2-enamide monohydrochloride); GABA modulators; modulators of neuronal potassium channels such as flupirtine and retigabine; and glutamate receptor modulators.

In one embodiment the pharmaceutical composition is administered in combination with other pharmaceutical compositions comprising levodopa that have immediate release and controlled release properties, to achieve a pharmacological active level of levodopa for a prolonged time such as approx. 1-8 hours. This will significantly reduce the dosing frequency for the majority of Parkinson's disease patients compared with currently used products.

In one embodiment the pharmaceutical composition is administered in combination with an immediate release product comprising levodopa, and/or administered in combination with a controlled release product comprising levodopa.

In one embodiment the pharmaceutical composition is administered in combination with one or more products selected from the group consisting of Sinemet, Pharmacopa, Atamet, Stalevo, Madopar, Prolopa, Parcopa, Lodosyn, Modopar, Madopark, Neodopasol, EC-Doparyl, Aldomet, Aldoril, Dopamet and Dopegyt.

In one embodiment the pharmaceutical composition as disclosed herein, and the further active pharmaceutical ingredient, are administered simultaneously, separately or sequentially.

Kit of Parts

The present disclosure also provides for a kit of parts which can be useful for treatment of morning akinesia as described herein.

A kit of parts according to the present disclosure comprises a pharmaceutical composition as defined herein for treatment, prevention or alleviation of morning akinesia. Kits allows for simultaneous, sequential or separate administration of the pharmaceutical composition and one or more further active pharmaceutical ingredients as described herein.

Examples

Example 1

Lactose was mixed with Microcrystalline cellulose, Sodium starch glycolate and a model compound (Nicotinamide) for 5 min. in a tumble mixer. Next magnesium stearate was added and mixed in for 30 sec. The mix was compressed to tablets, each tablet with a tablet weight of 6.6 mg and size 2 mm each holding 0.28 mg model compound. Tablet thickness was around 1.7 mm.

| | |
|---|---|
| Lactose | 183.20 |
| Microcrystalline cellulose | 76.00 |
| Sodium starch glycolate type A | 120.00 |
| Model compound | 16.80 |
| Magnesium stearate | 4.00 |
| Total | 400.00 |

Model compound mini-tablets were film-coated in a fluid bed with a semi-permeable film based on Ethyl cellulose. Film composition is given in the below table. For 325 g core tablets, 1000 g of film solution was produced to be able to film coat to the desired increase in tablet weight of up to 25.0% incl. 10% overage for production loss. Spraying conditions were controlled to an outlet air temperature of 28-30° C. To reach the desired weight gain of 20%, 23% and 25%, 682.0 g, 784.9 g and 853.1 g film solution was applied respectively.

| | |
|---|---|
| Ethyl cellulose 7 cps | 100.0 |
| Ethanol 96% | 900.0 |
| Total | 1000.0 |

Figure 2:
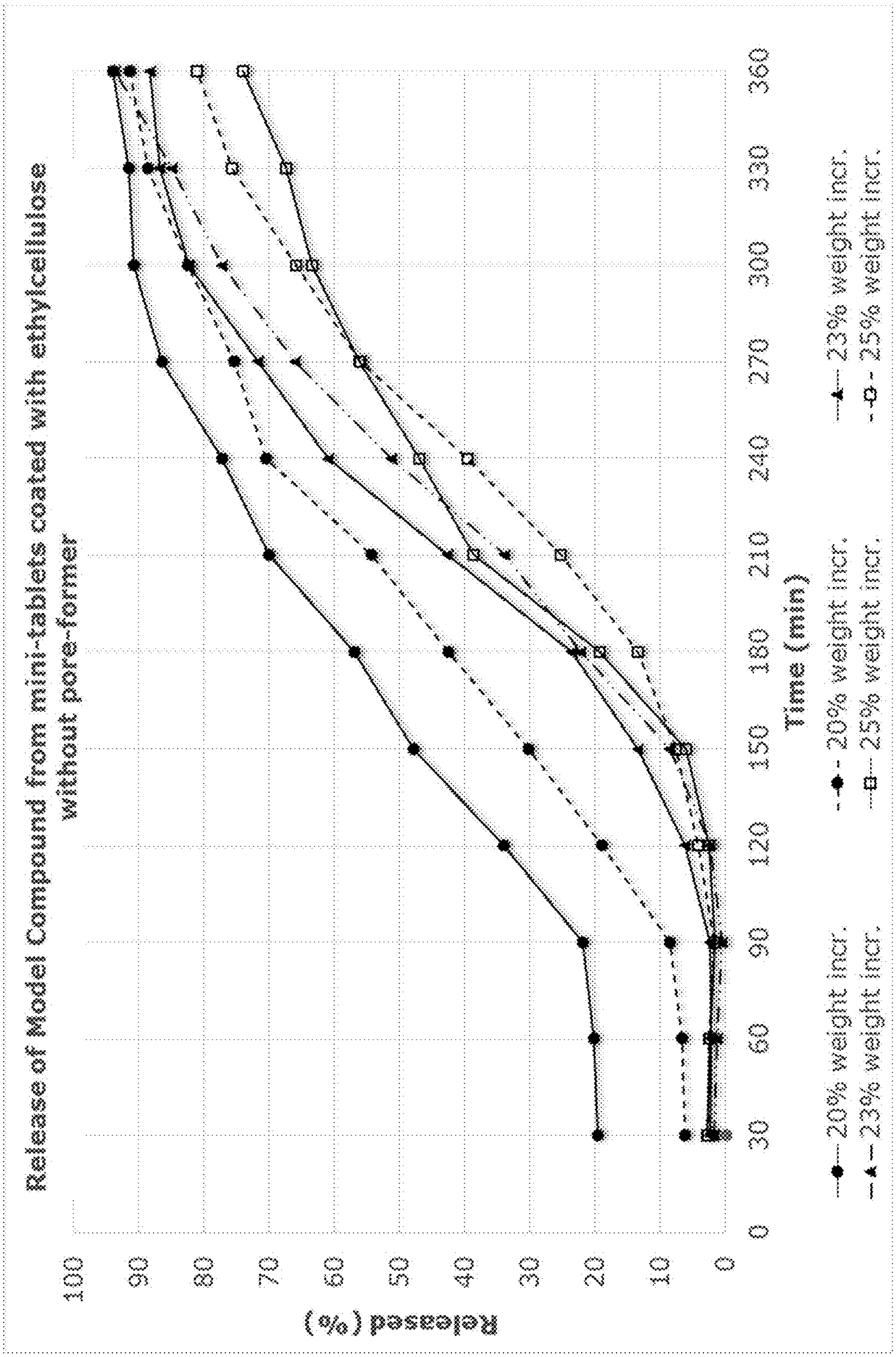
FIG. 2: Release of Model Compound: Mini-tablets with 30% Sodium starch glycolate coated with ethylcellulose film (20-25% weight increase): Lag-time achieved with release of 50% from 3 to 5 h with 25% coating. Some variation in data (see Example 1).

44 Mini-tablets were tested for dissolution using an USP2 Paddle apparatus (USP Paddle Dissolution Test Method). Each vessel contained 600 ml isotonic sodium chloride solution and was rotated at 75 rpm. Retrieved samples were quantified at a spectrophotometer at 260 nm. Results are shown in FIG. 2.

Example 2

Mini-tablets from Example 1 were film-coated in a fluid bed with a semi-permeable film based on Ethyl cellulose. Film composition is given in the below table. For 325 g core tablets, 1000 g of film solution was produced to be able to film coat to the desired increase in tablet weight of up to 25.0% incl. 10% overage for production loss. Spraying conditions were controlled to an outlet air temperature of 28-29° C. To reach the desired weight gain of 10%, 15%, 20% and 25%, 341.3 g, 511.9 g, 682.5 g and 853.1 g film solution was applied respectively.

| | |
|---|---|
| Ethyl cellulose 7 cps | 90.0 |
| Ethanol 96% | 675.0 |
| Polyvinyl alcohol | 10.0 |
| Purified water | 225.0 |
| Total | 1000.0 |

Figure 3A:
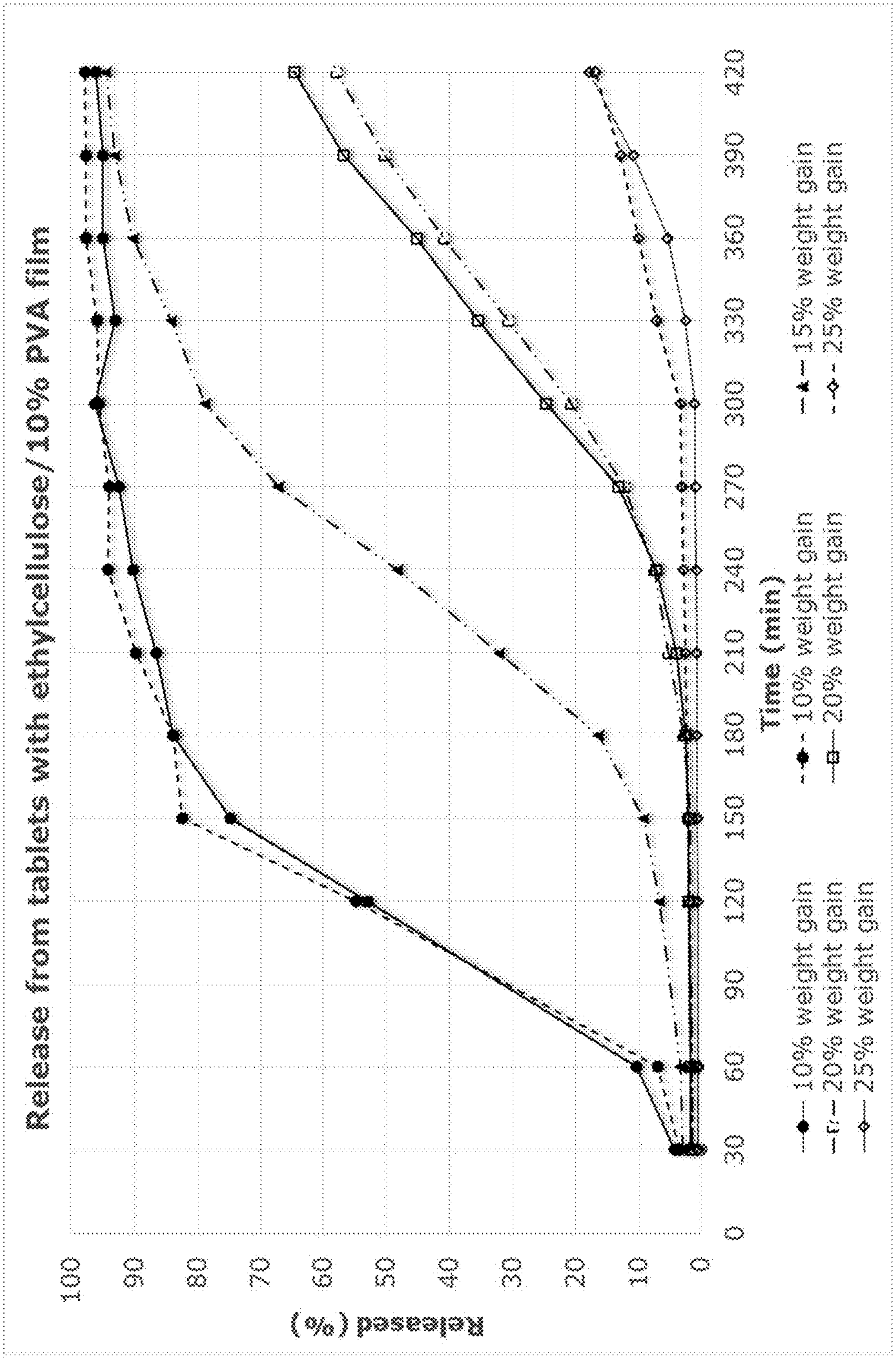
FIG. 3A: Release of Model Compound: 30% Sodium starch glycolate coated with ethylcellulose film (10-25% weight increase); 10% PVA added as pore former. Lag-time achieved with release of 65% from 3 to 5 h with 15% coating for 10% PVA.

44 Mini-tablets were tested for dissolution using an USP2 Paddle apparatus. Each vessel contained 600 ml isotonic sodium chloride solution and was rotated at 75 rpm. Retrieved samples were quantified at a spectrophotometer at 260 nm. Results are shown in FIG. 3A.

Example 3

Mini-tablets from Example 1 were film-coated as described in Example 2 with the following film composition:

| | |
|---|---|
| Ethyl cellulose 7 cps | 76.0 |
| Ethanol 96% | 678.7 |
| Polyvinyl alcohol | 19.01 |
| Purified water | 226.2 |
| Total | 1000.0 |

Figure 3B:
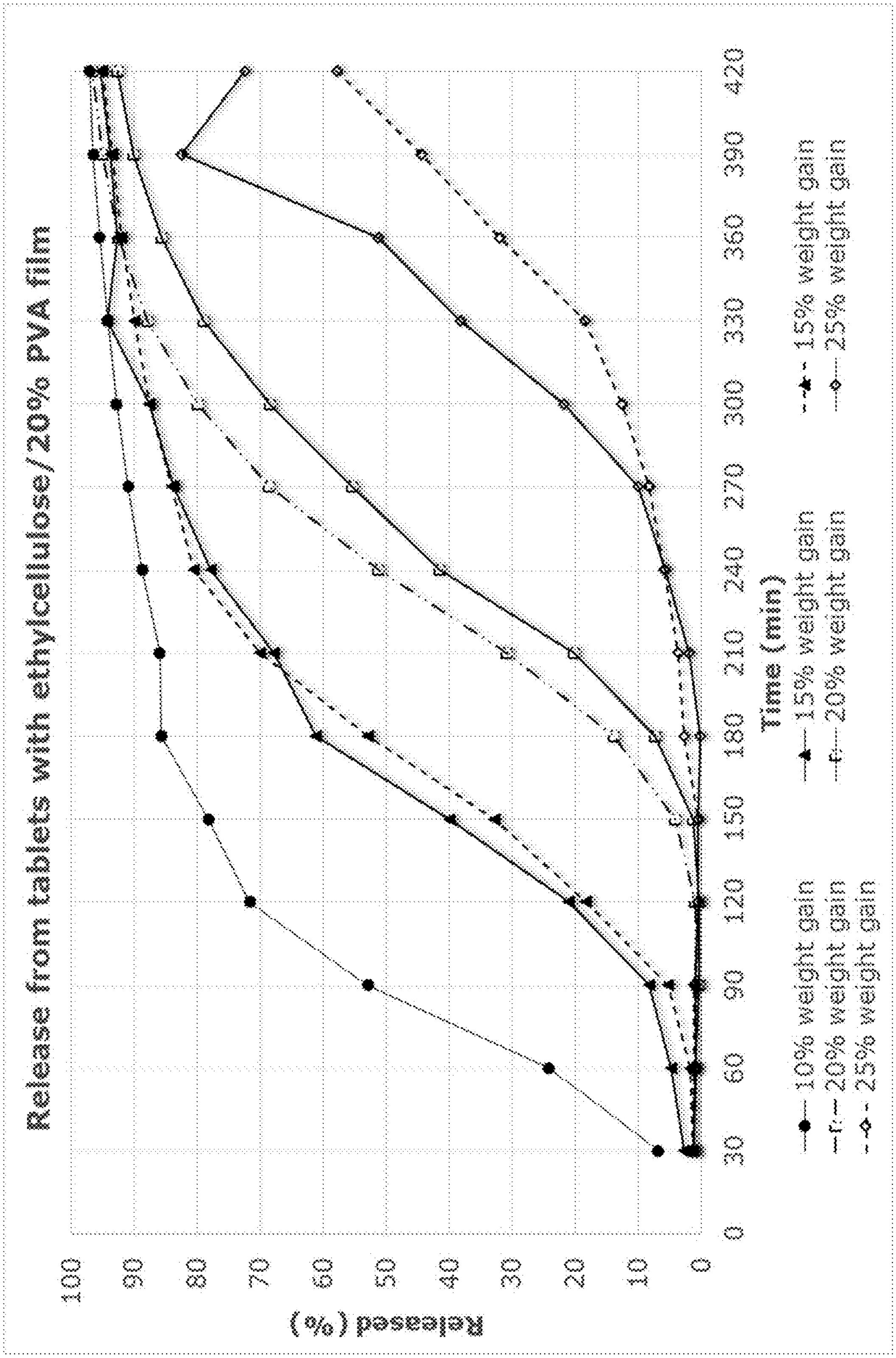
FIG. 3B: Release of Model Compound: 30% Sodium starch glycolate coated with ethylcellulose film (10-25% weight increase); 20% PVA added as pore former. Lag-time achieved with release of 70% from 3 to 5 h with 20% coating for 20% PVA. Less variation in data (see Examples 2 and 3).

The mini-tablets were tested as described in Example 2 and the results given in FIG. 3B.

Example 4

Mini-tablets from Example 1 were film-coated as described in Example 2 with the following film composition:

| | |
|---|---|
| Ethyl cellulose 7 cps | 90.0 |
| Ethanol 96% | 675.75 |
| Hypromellose 3 | 9.0 |
| Purified water | 225.25 |
| Total | 1000.0 |

Figure 4A:
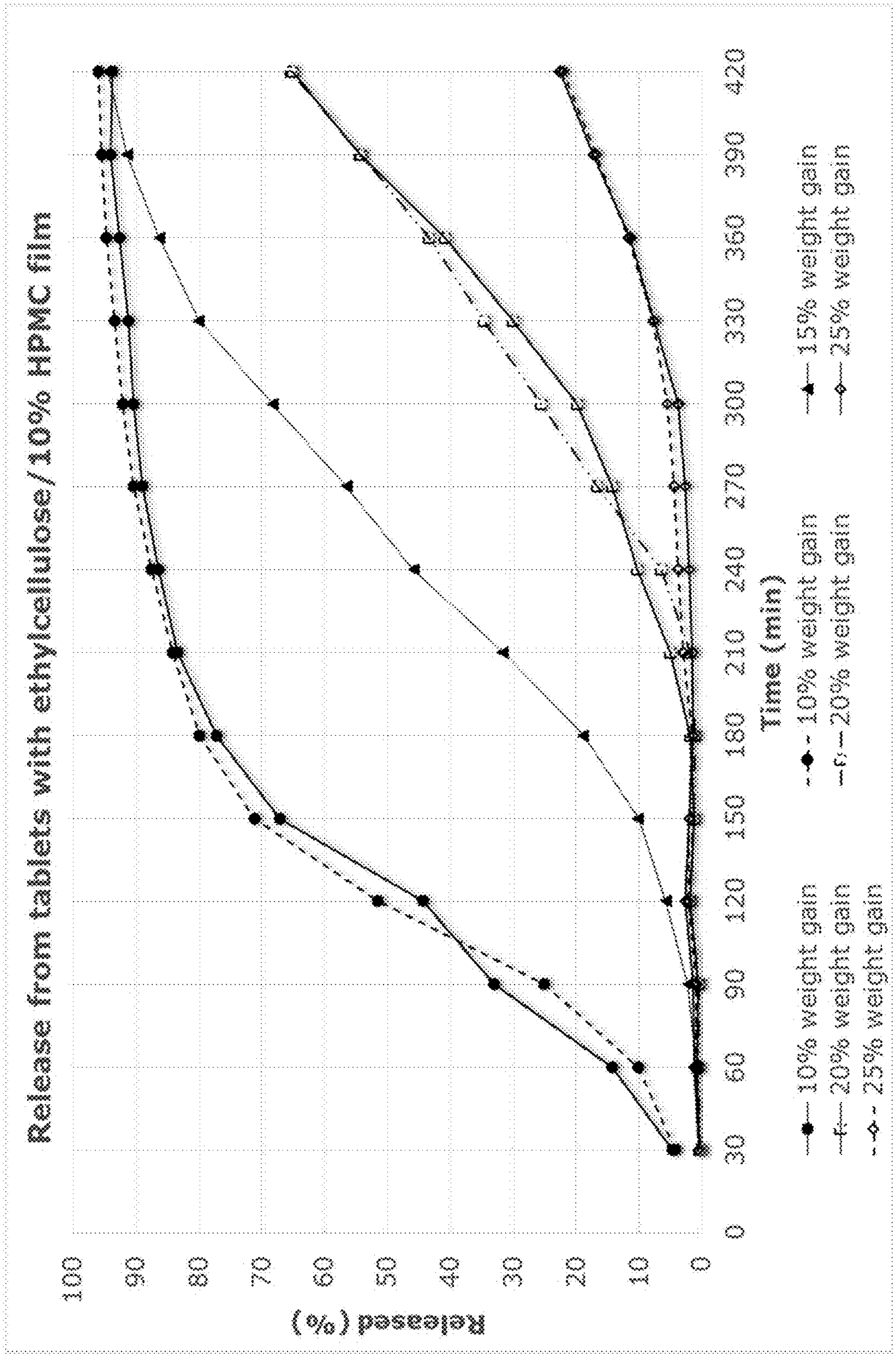
FIG. 4A: Release of Model Compound: 30% Sodium starch glycolate coated with ethylcellulose film (10-25% weight increase); 10% HPMC added as pore former. Lag-time achieved with release of 50% from 3 to 5 h with 15% coating for 10% HPMC. Increased film weight correlates with slower release/less burst; and increased pore former correlates with higher burst release. Low variation in data (see Examples 4 and 5).

The mini-tablets were tested as described in Example 2 and the results given in FIG. 4A.

Example 5

Mini-tablets from Example 1 were film-coated as described in Example 2 with the following film composition:

| | |
|---|---|
| Ethyl cellulose 7 cps | 80.0 |
| Ethanol 96% | 675.0 |
| Hypromellose 3 | 20.0 |
| Purified water | 225.0 |
| Total | 1000.0 |

Figure 4B:
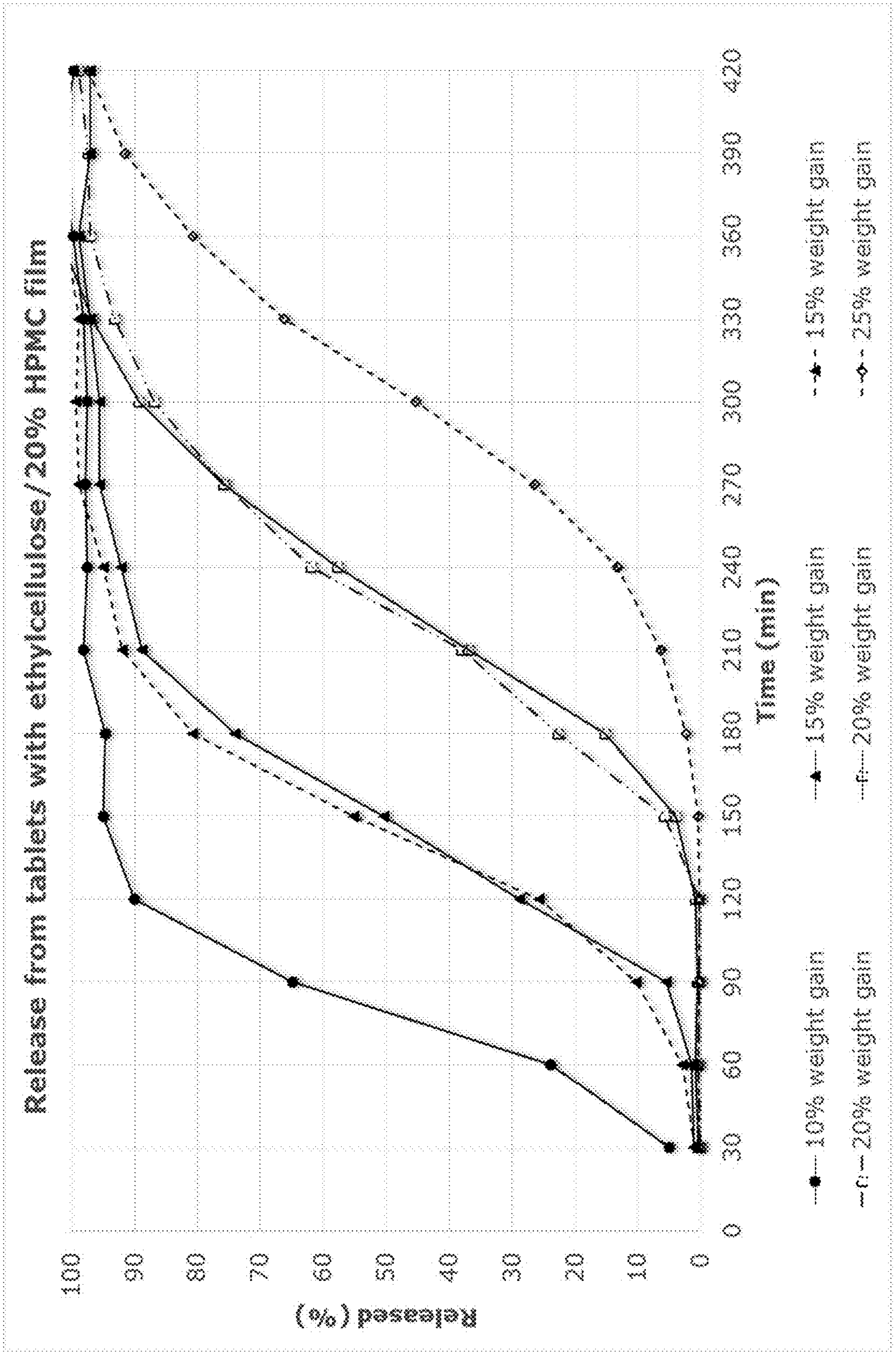
FIG. 4B: Release of Model Compound: 30% Sodium starch glycolate coated with ethylcellulose film (10-25% weight increase); 20% HPMC added as pore former. Lag-time achieved with release of 75% from 3 to 5 h with 20% coating for 20% HPMC. Increased film weight correlates with slower release/less burst; and increased pore former correlates with higher burst release. Low variation in data (see Examples 4 and 5).

The mini-tablets were tested as described in Example 2 and the results given in FIG. 4B.

Example 6

Levodopa was mixed with Microcrystalline cellulose, Sodium starch glycolate and Pre-gelatinized starch for 2 min. in a 1 L high shear mixer. Purified water was added slowly over 3-4 min. while mixing until proper humidity was achieved and then granulated for 2 min. The produced granulate was dried at 40° C. overnight and sieved through a 0.6 mm screen.

| | |
|---|---|
| Levodopa | 180.00 |
| Microcrystalline cellulose | 60.00 |
| Sodium starch glycolate type A | 30.00 |
| Pre-gelatinized starch | 30.00 |
| Purified water | qs (≈160 g) |
| Total | 300.0 |

The produced Levodopa granulate was mixed with Sodium starch glycolate and magnesium stearate.

| | |
|---|---|
| Levodopa granulate | 277.0 |
| Sodium starch glycolate type A | 80.91 |
| Magnesium stearate | 3.62 |
| Total | 361.53 |

The mix was compressed to tablets, each tablet with a tablet weight of 6.15 mg and size 2 mm each holding 2.8 mg Levodopa. Tablet thickness was around 1.7 mm.

| Composition | % | mg/tablet |
|---|---|---|
| Levodopa | 46.0% | 2.83 |
| Microcrystalline cellulose | 15.3% | 0.94 |
| Sodium starch glycolate Type A | 30.0% | 1.85 |
| Pregelatinized starch | 7.7% | 0.47 |
| Mg. Stearat | 1.0% | 0.06 |
| Total | | 6.15 |

Levodopa mini-tablets were film-coated in a fluid bed with a semi-permeable film based on Ethyl cellulose. Film composition is given in the below table. For 320 g core tablets, 900 g of film solution was produced to be able to film coat to the desired increase in tablet weight of up to 25.0% incl. 10% overage for production loss. Spraying conditions were controlled to an outlet air temperature of 27-29° C. To reach the desired weight gain of 10%, 15%, 20% and 25%, 336.0 g, 504.0 g, 672.0 g and 840.0 g film solution was applied respectively.

| | |
|---|---|
| Ethyl cellulose 7 cps | 72.0 |
| Ethanol 96% | 607.5 |
| Hypromellose 3 cps | 18.0 |
| Purified water | 202.5 |
| Total | 900.0 |

100 mg Levodopa corresponds to approx. 35 mini-tablets.

Example 7

Levodopa was mixed with Microcrystalline cellulose, Sodium starch glycolate and Pre-gelatinized starch for 2 min. in a 1 L high shear mixer. Purified water was added slowly over 3-4 min. while mixing until proper humidity was achieved and then granulated for 2 min. The produced granulate was dried at 40° C. overnight and sieved through a 0.6 mm screen.

| | |
|---|---|
| Levodopa | 195.00 |
| Microcrystalline cellulose | 60.00 |
| Sodium starch glycolate type A | 15.00 |
| Pre-gelatinized starch | 30.00 |
| Purified water | qs (≈160 g) |
| Total | 300.0 |

The produced Levodopa granulate was mixed with Sodium starch glycolate and magnesium stearate. The mix was compressed to tablets, each tablet with a tablet weight of 6.4 mg and size 2 mm each holding 3.0 mg Levodopa. Tablet thickness was around 1.7 mm

| | |
|---|---|
| Levodopa granulate | 254.03 |
| Sodium starch glycolate type A | 92.47 |
| Magnesium stearate | 3.50 |
| Total | 350.0 |

Levodopa mini-tablets were film-coated in a fluid bed with a semi-permeable film based on Ethyl cellulose. Film composition is given in the below table. For 300 g core tablets, 900 g of film solution was produced to be able to film coat to the desired increase in tablet weight of up to 25.0% incl. 10% overage for production loss. Spraying conditions were controlled to an outlet air temperature of 27-29° C. To reach the desired weight gain of 17.5%, 20.0%, 22.5% and 25.0%, 551.3 g, 630.0 g, 708.8 g and 787.5 g film solution was applied respectively.

| | |
|---|---|
| Ethyl cellulose 7 cps | 72.0 |
| Ethanol 96% | 607.5 |
| Hypromellose 3 cps | 18.0 |
| Purified water | 202.5 |
| Total | 900.0 |

100 mg Levodopa corresponds to approx. 33 mini-tablets.

Example 8

Figure 6:
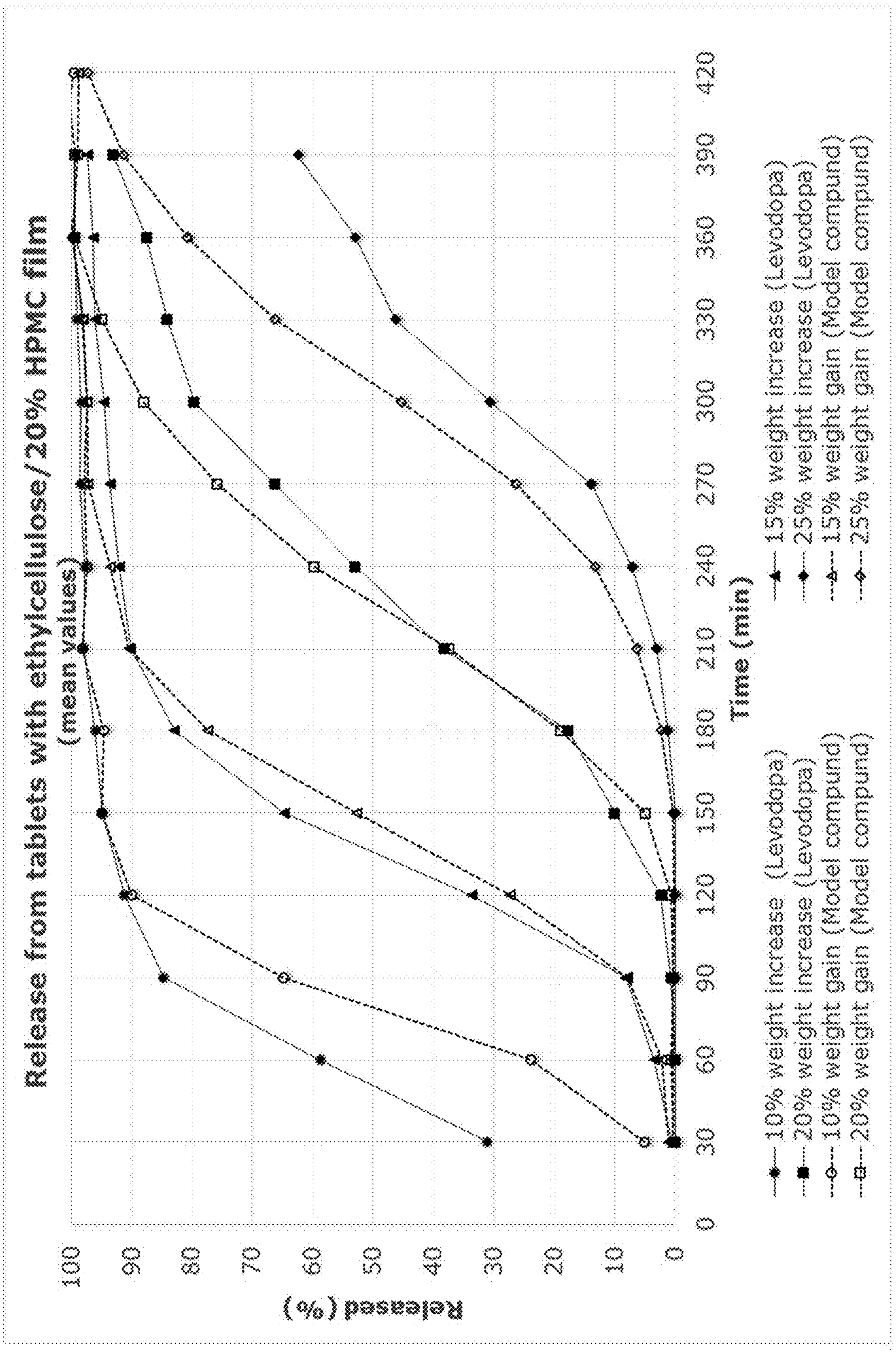
FIG. 6: Levodopa release: Mini-tablets with 30% Sodium starch glycolate coated with ethylcellulose film (10-25% weight increase); 20% HPMC added as pore former. Release from Levodopa mini-tablets is well controlled. Data from release of Model compound included to demonstrate similar release patterns (see Example 8).

Mini-tablets from Example 6 were tested for dissolution using an USP2 Paddle apparatus. Mini-tablets corresponding to 100 mg Levodopa were tested in each vessel using 600 ml isotonic sodium chloride solution and 75 rpm. Retrieved samples were quantified at a spectrophotometer at 284 nm. Results are shown in FIG. 6 (full lines) together with results from Example 5 (dotted lines) to demonstrate similar release from Levodopa compared to model compound.

Example 9

Figure 5:
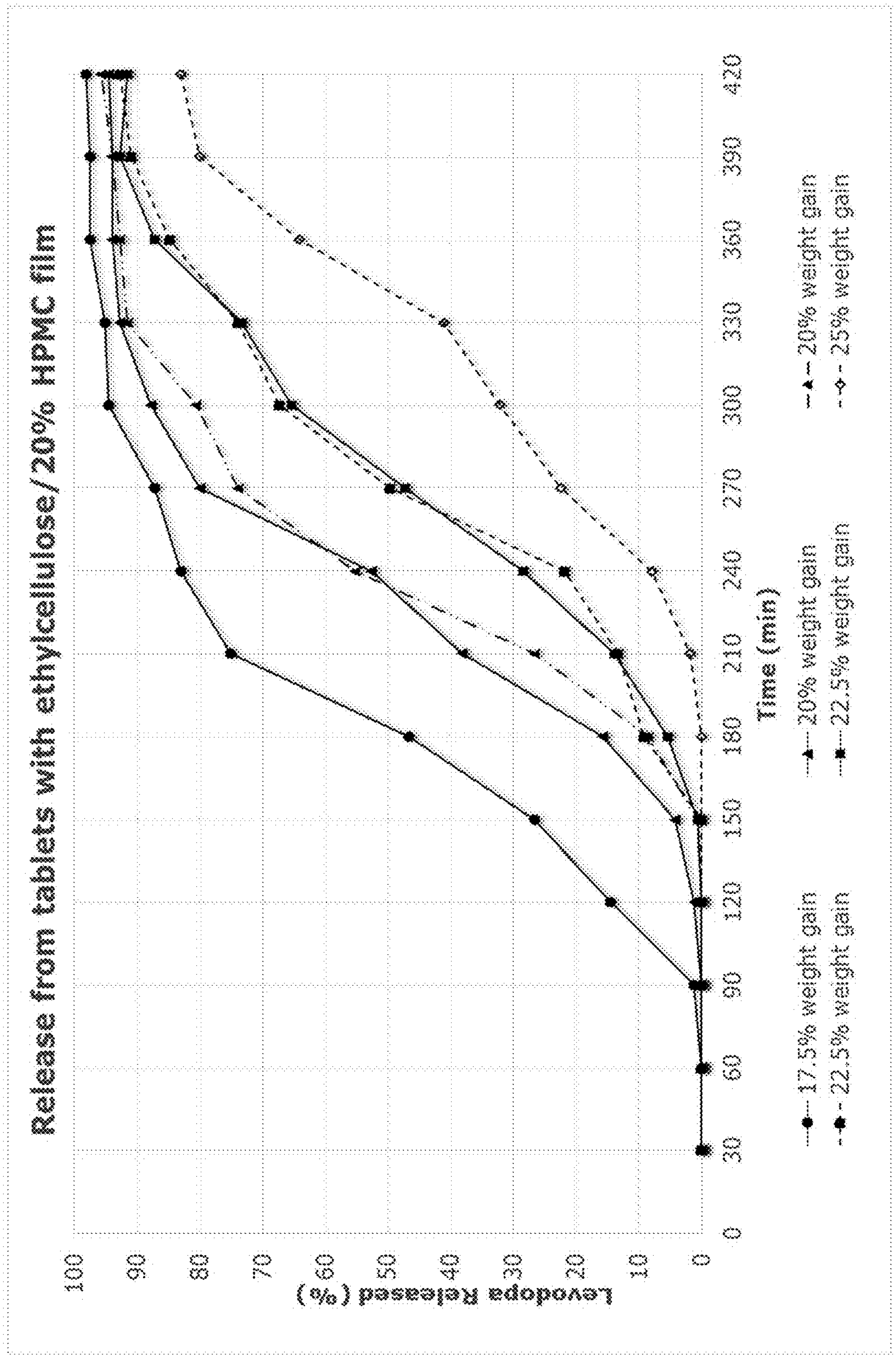
FIG. 5: Levodopa release: Mini-tablets with 30% Sodium starch glycolate coated with ethylcellulose film (17.5-25% weight increase); 20% HPMC added as pore former. Release from Levodopa mini-tablets is well controlled (see Example 9).

Mini-tablets from Example 7 were tested for dissolution using an USP2 Paddle apparatus. Mini-tablets corresponding to 100 mg Levodopa were tested in each vessel using 600 ml isotonic sodium chloride solution and 75 rpm. Retrieved samples were quantified at a spectrophotometer at 284 nm. Results are shown in FIG. 5.

Example 10

Levodopa was mixed with Microcrystalline cellulose, Sodium starch glycolate and Pre-gelatinized starch for 2 min. in a 1 L high shear mixer. Purified water was added slowly over 3-4 min. while mixing until proper humidity was achieved and then granulated for 2 min. The produced granulate was dried at 40° C. overnight and sieved through a 0.6 mm screen.

| | |
|---|---|
| Levodopa | 225.00 |
| Microcrystalline cellulose | 30.00 |
| Sodium starch glycolate type A | 15.00 |
| Pre-gelatinized starch | 30.00 |
| Purified water | qs (≈110 g) |
| Total | 300.0 |

The produced Levodopa granulate was mixed with Sodium starch glycolate and magnesium stearate. The mix was compressed to tablets, each tablet with a tablet weight of 5.75 mg and size 2 mm each holding 4.0 mg Levodopa. Tablet thickness was around 1.6 mm

| | |
|---|---|
| Levodopa granulate | 292.22 |
| Sodium starch glycolate type A | 16.66 |
| Magnesium stearate | 3.12 |
| Total | 312.0 |

Levodopa mini-tablets were film-coated in a fluid bed with a semi-permeable film as described in Example 6. 100 mg Levodopa corresponds to approx. 44 mini-tablets.

Figure 7:
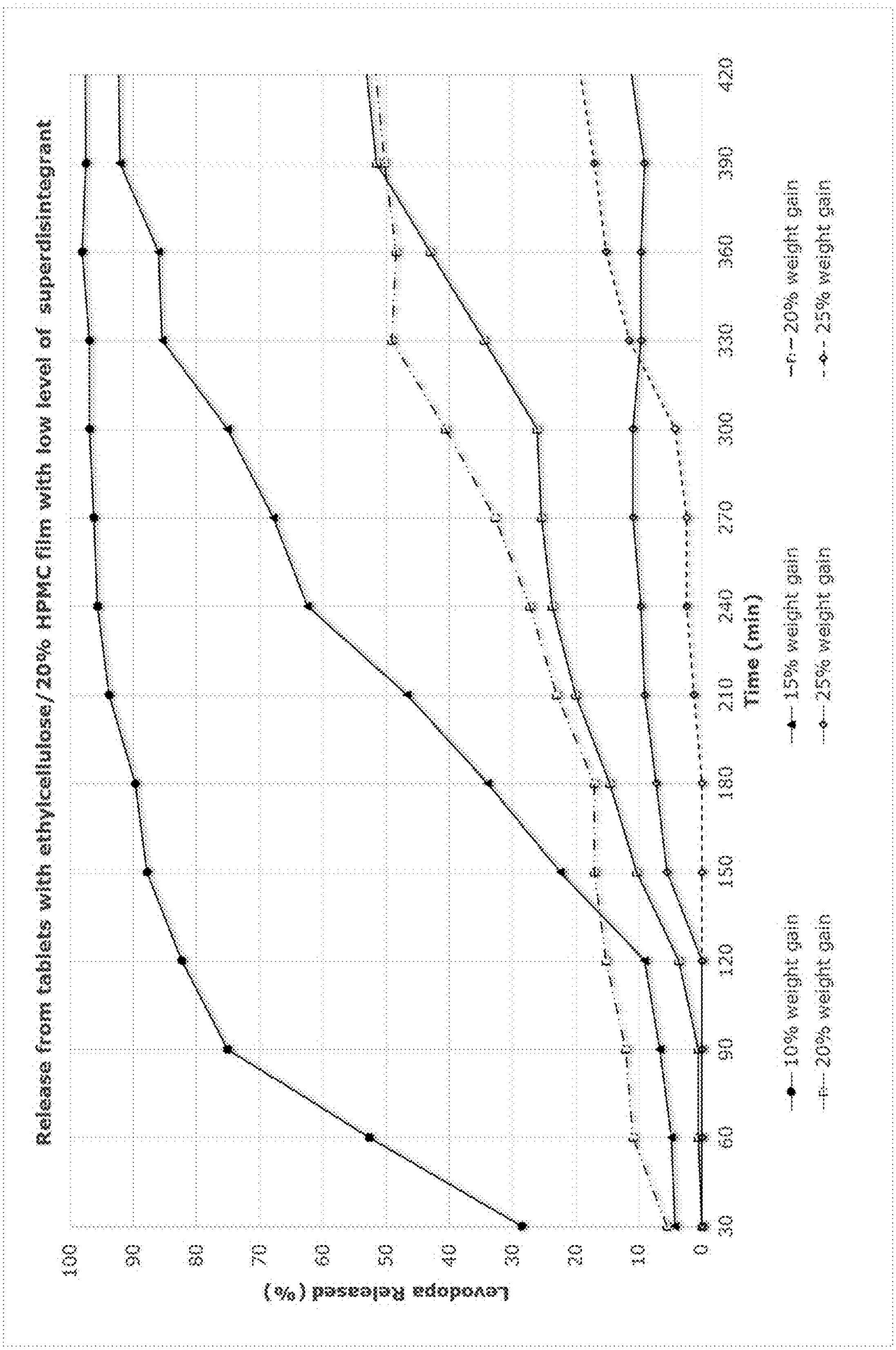
FIG. 7: Levodopa release: Mini-tablets with 10% Sodium starch glycolate coated with ethylcellulose film (10-25% weight increase); 20% HPMC added as pore former. Release from Levodopa mini-tablets with low level of super disintegrant is not well controlled and display poor burst release (see Example 10).

Mini-tablets were tested for dissolution as described in Example 8 and results are given in FIG. 7 demonstrating poor control and poor burst release with low level super disintegrant.

Example 11

Carbidopa is mixed with Microcrystalline cellulose, Sodium starch glycolate and pre-gelatinized starch for 2 min. in a 1 L high shear mixer. Purified water is added slowly over 3-4 min. while mixing until proper humidity was achieved and then granulated for 2 min. The produced granulate is dried at 40° C. overnight and sieved through a 0.6 mm screen.

| | |
|---|---|
| Carbidopa | 100.00 |
| Microcrystalline cellulose | 70.00 |
| Sodium starch glycolate type A | 10.00 |
| Pre-gelatinized starch | 20.00 |
| Purified water | qs (≈70 g) |
| Total | 200.0 |

The produced Carbidopa granulate is mixed with Sodium starch glycolate and magnesium stearate. The mix is compressed to tablets, each tablet with a tablet weight of 6.90 mg and size 2 mm each holding 2.5 mg Carbidopa. Tablet thickness is around 1.9 mm.

| | |
|---|---|
| Carbidopa granulate | 217.74 |
| Sodium starch glycolate type A | 79.26 |
| Magnesium stearate | 3.00 |
| Total | 300.0 |

Carbidopa mini-tablets are film-coated in a fluid bed with a semi-permeable film based on Ethyl cellulose. Film composition is given in the below table. For 300 g core tablets, 900 g of film solution is produced to be able to film coat to the desired increase in tablet weight of up to 25.0% incl. 10% overage for production loss. Spraying conditions are controlled to an outlet air temperature of 27-29° C. To reach the desired weight gain of 10%, 15%, 20% and 25%, 336.0 g, 504.0 g, 672.0 g and 840.0 g film solution is applied respectively.

| | |
|---|---|
| Ethyl cellulose 7 cps | 72.0 |
| Ethanol 96% | 607.5 |
| Hypromellose 3 cps | 18.0 |
| Purified water | 202.5 |
| Total | 900.0 |

25 mg Carbidopa corresponds to approx. 10 mini-tablets.

Example 12

Mini-tablets from Example 11 are tested for dissolution using an USP2 Paddle apparatus. Mini-tablets corresponding to 25 mg Carbidopa are tested in each vessel using 600 ml isotonic sodium chloride solution and 75 rpm. Retrieved samples are quantified at a spectrophotometer at 284 nm.

Example 13

33 Levodopa mini-tablets coated to 25% weight gain from Example 7 and ten film coated Carbidopa mini-tablets from Example 11 are mixed and filled into a hard shell gelatine capsule size 0. The capsule holds a dose of 100 mg Levodopa+25 mg Carbidopa and the active components will be released after a lag-time; Carbidopa will be released followed by Levodopa.

Example 14

Morning Akinesia, Phase 1 PK Study

A randomized, open-label, cross-over study evaluating the pharmacokinetic characteristics and relative bioavailability of single dosings of a number of selected prototype formulations containing carbidopa and L-DOPA in healthy subjects.

The primary endpoint is to evaluate the pharmacokinetic (PK) characteristics and relative bioavailability of single dosings of a number of selected prototype pulsatile release formulations containing carbidopa and L-DOPA.

The following evaluations will be made:

Concentration-time data from plasma will be used to calculate applicable PK parameters for L-DOPA and carbidopa, including maximum plasma level (Cmax and Tmax).

Example 15

Morning Akinesia, Phase Ib, efficacy/safety and PK study

A randomized, double-blinded, placebo-controlled, cross-over study evaluating the short term efficacy and safety as well as the pharmacokinetic characteristics of single dosing of a number of selected prototype formulations containing carbidopa and L-DOPA in patients with Parkinson's disease suffering from morning akinesia.

The primary endpoint is to evaluate the efficacy (short term) of single dosing of a number of selected prototype pulsatile release formulations containing carbidopa and L-DOPA.

The following evaluations will be made:

Assessment of the Parkinson's disease symptoms at morning time when morning akinesia is usually present (by the use of the UPDRS scale) after treatment with the selected prototype formulations containing carbidopa and L-DOPA.

Example 16

Carbidopa was mixed with Microcrystalline cellulose, Sodium starch glycolate and Pre-gelatinized starch for 2 min. in a 1 L high shear mixer. A solution of Pre-gelatinized starch in Purified water was added slowly over 2-3 min. while mixing until proper humidity is achieved and then granulated for 1 min. The produced granulate is dried in a STREA fluid-bed at approx. 60° C. until water activity was below 20% and sieved through a 1.4 mm screen.

| | |
|---|---|
| Carbidopa | 75.00 |
| Microcrystalline cellulose | 31.95 |
| Sodium starch glycolate type A | 28.05 |
| Pre-gelatinized starch | 10.00 |
| Purified water | 121 |
| Pre-gelatinized starch | 5.00 |
| Total | 150.0 |

The produced Carbidopa granulate was mixed with Sodium starch glycolate and magnesium stearate. The mix was compressed to tablets, each tablet with a tablet weight of approx. 7.20 mg and size 2 mm each holding 2.6 mg Carbidopa. Tablet thickness was around 1.8 mm.

| | |
|---|---|
| Carbidopa granulate | 254.10 |
| Sodium starch glycolate type A | 92.49 |
| Magnesium stearate | 3.50 |
| Total | 350.0 |

Carbidopa mini-tablets were film-coated in a fluid bed with a semi-permeable film based on Ethyl cellulose. Film composition is given in the below table. For 300 g core tablets, 900 g of film solution was produced to be able to film coat to the desired increase in tablet weight of up to 25.0% incl. 5% overage for production loss. Spraying conditions were controlled to an outlet air temperature of 27-29° C. To reach the desired weight gain of 15%, 17.5%, 20%, 22.5% and 25%, 441.0 g, 514.5 g, 588.0 g, 661.5 g and 735.0 g film solution was applied respectively.

| | |
|---|---|
| Ethyl cellulose 7 cps | 72.0 |
| Ethanol 96% | 607.5 |
| Hypromellose 3 cps | 18.0 |
| Purified water | 202.5 |
| Total | 900.0 |

25 mg Carbidopa corresponds to approx. 10 mini-tablets.

Example 17

Figure 8:
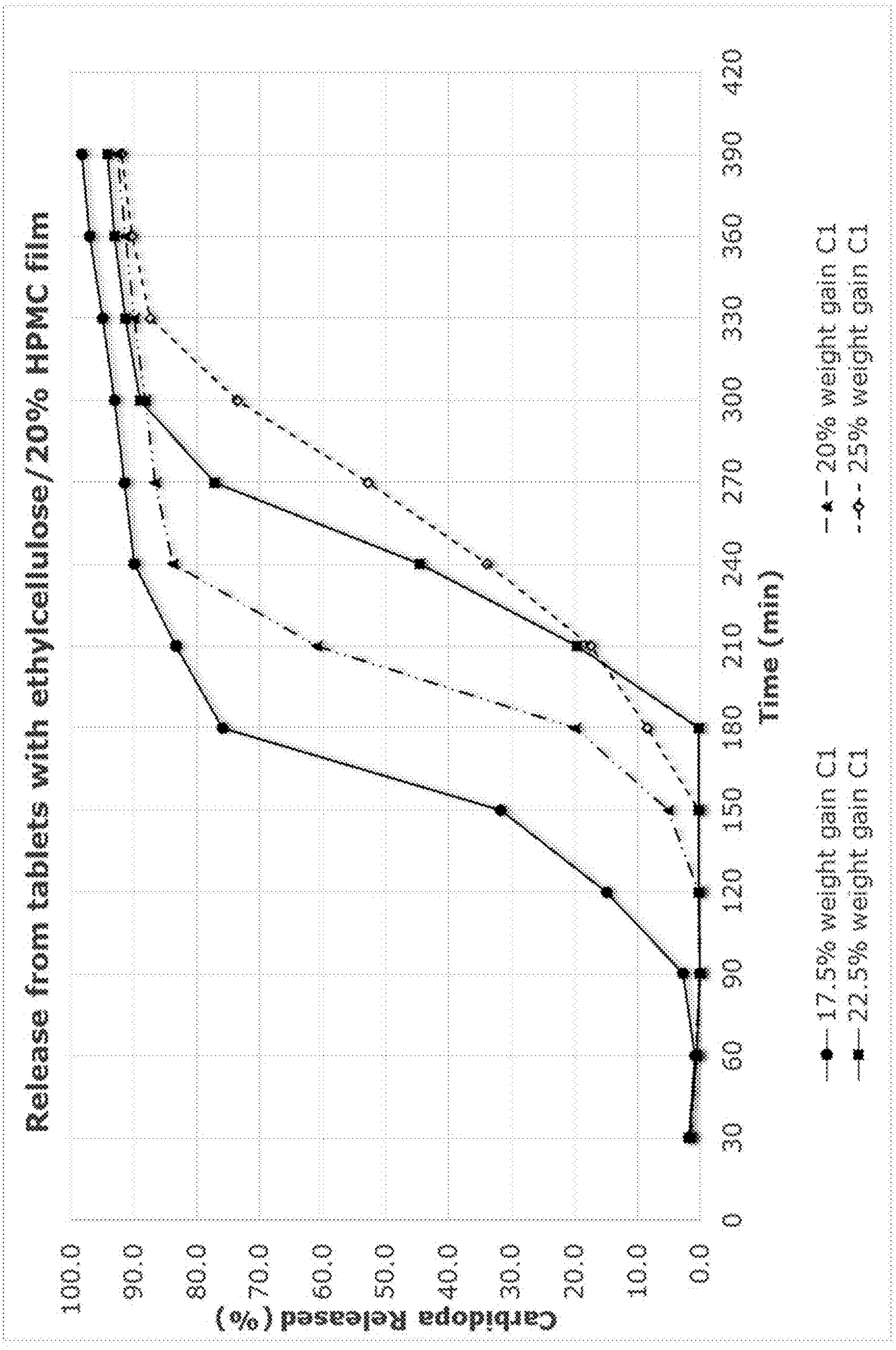
FIG. 8: Carbidopa release: Mini-tablets with 40% Sodium starch glycolate coated with ethylcellulose film (17.5-25% weight increase); 20% HPMC added as pore former. Release from Carbidopa mini-tablets is well controlled (see Example 17).

Mini-tablets from Example 16 were tested for dissolution using an USP2 Paddle apparatus. Mini-tablets corresponding to 25 mg Carbidopa were tested in each vessel using 600 ml isotonic sodium chloride solution and 75 rpm. Retrieved samples were quantified at a spectrophotometer at 284 nm. Results are shown in FIG. 8.

What is claimed is:

1. A method of treating morning akinesia in a Parkinson's disease patient in need of treatment of morning akinesia, the method consisting of orally administering to the patient, once daily, 0 to 4 hours prior to bedtime, a pharmaceutical composition consisting of one dose of levodopa that is about 100 mg, one dose of carbidopa that is about 25 mg, and one or more excipients;

wherein the pharmaceutical composition provides for a levodopa off-release lag time of 3 to 7 hours and a carbidopa off-release lag time of 3 to 7 hours in the patient after the oral administration of the pharmaceutical composition; and wherein the one dose of the levodopa is released from the pharmaceutical composition in one pulsatile release only after the levodopa off-release lag time; and the one dose of the carbidopa is released from the pharmaceutical composition in one pulsatile release only after the carbidopa off-release lag time.

2. The method of claim 1, wherein the pharmaceutical composition is administered 0 to 3 hours prior to bedtime.

3. The method of claim 1, wherein the pharmaceutical composition is administered 0 to 2 hours prior to bedtime.

4. The method of claim 1, wherein the pharmaceutical composition is administered 0 to 1 hours prior to bedtime.

5. The method of claim 1, wherein the pharmaceutical composition provides for a carbidopa off-release lag time of about 7 hours after the oral administration of the pharmaceutical composition.

6. The method of claim 1, wherein the pharmaceutical composition provides for a carbidopa off-release lag time of about 6 hours after the oral administration of the pharmaceutical composition.

7. The method of claim 1, wherein the pharmaceutical composition provides for a carbidopa off-release lag time of about 5 hours after the oral administration of the pharmaceutical composition.

8. The method of claim 1, wherein the pharmaceutical composition provides for a carbidopa off-release lag time of about 4 hours after the oral administration of the pharmaceutical composition.

9. The method of claim 1, wherein the pharmaceutical composition provides for a carbidopa off-release lag time of about 3 hours after the oral administration of the pharmaceutical composition.

10. The method of claim 1, wherein in said pulsatile release of the one dose of levodopa, 70 to 100% of the one dose of the levodopa is released from the pharmaceutical composition within 2 hours after the levodopa off-release lag time, and in said pulsatile release of the one dose of carbidopa, 70 to 100% of the amount of the one dose of carbidopa is released from the pharmaceutical composition within 2 hours after the carbidopa off-release lag time.

* * * * *